US008546524B2

(12) United States Patent
Tarasova et al.

(10) Patent No.: US 8,546,524 B2
(45) Date of Patent: Oct. 1, 2013

(54) SMOOTHENED POLYPEPTIDES AND METHODS OF USE

(75) Inventors: Nadya Tarasova, Frederick, MD (US); Michael Dean, Frederick, MD (US); Hong Lou, Frederick, MD (US)

(73) Assignee: The United States of America, as represented by the Secretary, Department of Health and Human Services, Bethesda, MD (US)

( * ) Notice: Subject to any disclaimer, the term of this patent is extended or adjusted under 35 U.S.C. 154(b) by 0 days.

(21) Appl. No.: 13/470,965

(22) Filed: May 14, 2012

(65) Prior Publication Data

US 2012/0282196 A1    Nov. 8, 2012

Related U.S. Application Data

(63) Continuation of application No. 12/513,091, filed as application No. PCT/US2007/083027 on Oct. 30, 2007, now Pat. No. 8,198,402.

(60) Provisional application No. 60/855,422, filed on Oct. 31, 2006.

(51) Int. Cl.
*A61K 38/00*     (2006.01)
*A61P 35/00*     (2006.01)

(52) U.S. Cl.
USPC ........... 530/300; 514/1.1; 514/19.2; 514/19.3

(58) Field of Classification Search
None
See application file for complete search history.

(56) References Cited

U.S. PATENT DOCUMENTS

| | | | |
|---|---|---|---|
| 4,450,150 A | 5/1984 | Sidman | |
| 5,087,616 A | 2/1992 | Myers et al. | |
| 5,449,752 A | 9/1995 | Fujii et al. | |
| 6,864,229 B2 | 3/2005 | Kuliopolis et al. | |
| 7,084,249 B1 | 8/2006 | Eisenbach et al. | |
| 2007/0271630 A1 | 11/2007 | Boukharov et al. | |
| 2010/0093625 A1 | 4/2010 | Tarasova et al. | |

FOREIGN PATENT DOCUMENTS

| | | | |
|---|---|---|---|
| WO | WO 99/01468 A2 | 1/1999 | |
| WO | WO 2004111636 A2 | * 12/2004 | |
| WO | WO 2006/052723 A2 | 5/2006 | |

OTHER PUBLICATIONS

Bowie, et al. Science, vol. 247: 1306-1310, 1990.*
Lazar, et al. Mol. Cell. Biol., 8(3): 1247-1252, 1988.*
Burgess, et al. J. Cell Biol. 111: 2129-2138, 1990.*
Ngo et al., in"The Protein Folding Problem and Tediary Structure Prediction", 1994, Merz, et al. (ed.), Birkhauser, Boston, MA, pp. 433, and 492-495.*
Sudarsanam, Proteins: Structure, Function, and Genetics, 1998, 30:228-231.*
Pan et al., J. Protein Chem., 1999, 18(5): 579-584.*
Beachy et al., "Tissue repair and stem cell renewal in carcinogenesis," *Nature*, 432, 324-331 (2004).
Berman et al., "Medulloblastoma growth inhibition by hedgehog pathway blockade," *Science*, 297, 1559-1561 (2002).
Berman et al., "Widespread requirement for Hedgehog ligand stimulation in growth of digestive tract tumours," *Nature*, 425, 846-851 (2003).
Bowie et al., *Science 247*, 1306-1310 (1990).
Burgess et al., *J. Cell Biol.*, 111, 2129-2138 (1990).
Covic et al., "Activation and inhibition of G protein-coupled receptors by cell-penetrating membrane-tethered peptides," *Proc. Natl. Acad. Sci.*, 99 (2), 643-648 (2002).
Deshayes et al., "Cell-penetrating peptides: tools for intracellular delivery of therapeutics," *Cell. Mol. Life Sci.*, 62, 1839-1849 (2005).
Douard et al., "Sonic Hedgehog-dependent proliferation in a series of patients with colorectal cancer," *Surgery*, 139 (5), 665-670 (2006).
El-Andaloussi et al., "Cell-penetrating peptides: mechanisms and applications," *Curr. Pharm. Design*, 11 (28), 3597-3611 (2005).
Fahy et al., "A comprehensive classification system for lipids," *J. Lipid Res.*, 46, 839-861 (2005).
GenBank Accession No. NM_000193 (Downloaded Apr. 28, 2009).
GenBank Accession No. NM_000264 (Downloaded Apr. 28, 2009).
GenBank Accession No. NM_001034190 (Downloaded Apr. 28, 2009).
GenBank Accession No. NM_005269 (Downloaded Apr. 28, 2009).
GenBank Accession No. NM_005270 (Downloaded Apr. 28, 2009).
GenBank Accession No. NM_005631 (Downloaded Apr. 28, 2009).
GenBank Accession No. NM_016701 (Downloaded Apr. 28, 2009).
Granier et al., "A cyclic peptide mimicking the third intracellular loop of the V2 vasopressin receptor inhibits signaling through its interaction with receptor dimer and G protein," *J. Biol. Chem. 279* (49), 50904-50914 (2004).
Hudecz, "Synthesis of peptide bioconjugates," *Methods Mol. Biol.*, 298, 209-223 (2005).
International Bureau of WIPO, *International Preliminary Report on Patentability*, from PCT/US2007/083027, mailed May 14, 2009.
Katano, "Hedgehog signaling pathway as a therapeutic target in breast cancer," *Cancer Lett.*, 227, 99-104 (2005).

(Continued)

*Primary Examiner* — Hong Sang
(74) *Attorney, Agent, or Firm* — Leydig, Voit & Mayer

(57) ABSTRACT

Disclosed is an isolated or purified polypeptide or peptidomimetic comprising an amino acid sequence of a portion of a Smoothened (SMO) protein, wherein the portion comprises an amino acid sequence of any of the intracellular loops of the SMO protein, a functional fragment thereof, or a functional variant of either the portion or the functional fragment, wherein the functional fragment comprises at least 7 contiguous amino acids of the intracellular loops, and wherein the functional fragment or functional variant inhibits proliferation of a diseased cell, or a fatty acid derivative thereof. Related conjugates, nucleic acids, recombinant expression vectors, host cells, and pharmaceutical compositions are further provided. Methods of inhibiting proliferation of a diseased cell, treating or preventing cancer, treating a neoplasm or psoriasis, and inhibiting the expression of genes involved in the Hedgehog signaling pathway, thereby inhibiting the Hedgehog signaling pathway, are furthermore provided by the invention.

46 Claims, 10 Drawing Sheets

(56) References Cited

OTHER PUBLICATIONS

Kirin et al., "Amino acid and peptide bioconjugates of copper(II) and zinc(II) complexes with a modified N,N-bis(2-picolyl)amine ligand," *Inorg. Chem.*, 44 (15), 5405-5415 (2005).

Lam et al., "A frequent activated smoothened mutation in sporadic basal cell carcinomas," *Oncogene*, 18, 833-836 (1999).

Lazar et al., *Mol. Cell. Biol.*, 8 (3), 1247-1252 (1988).

Mäe et al., "Cell-penetrating peptides as vectors for peptide, protein and oligonucleotide delivery," *Curr. Opin. Pharmacol.*, 6, 509-514 (2006).

Ngo et al., in "*The Protein Folding Problem and Tediary Structure Prediction*," 1994, Merz et al., (ed.), Birkhauser, Boston, MA, p. 433, and 492-495.

Pan et al., *J. Protein Chem*, 18(5), 579-584 (1999).

Pons et al., "Molecular biology of malignant melanoma and other cutaneous tumors," *Clin. Transl. Oncol.*, 8, 466-474 (2006).

Remsberg et al., "Structural analogues of smoothened intracellular loops as potent inhibitors of Hedgehog pathway and cancer cell growth," *J. Med. Chem.*, 50 (18), 4534-4538 (2007).

Romer et al., "Targeting medulloblastoma: small-molecule inhibitors of the Sonic Hedgehog pathway as potential cancer therapeutics," *Cancer Res.*, 65 (12), 4975-4978 (2005).

Sanchez et al., "Inhibition of prostate cancer proliferation by interference with Sonic Hedgehog-GLI1 signaling," *Proc. Natl. Acad. Sci.*, 101 (34), 12561-12566 (2004).

Sicklick et al., "Dysregulation of the Hedgehog pathway in human hepatocarcinogenesis," *Carcinogenesis*, 27 (4), 748-757 (2006).

Sudarsanam, *Proteins: Structure, Function, and Genetics*, 30, 228-231 (1998).

Tarasov et al., "Bisimidazoacridones: 2. Steady-state and time-resolved fluorescence studies of their diverse interactions with DNA," *Photochem. Photobiol.*, 78 (4), 313-322 (2003).

Tarasov et al., "Bisimidazoacridones: effect of molecular environment on conformation and photophysical properties," *Photochem. Photobiol.*, 70 (4), 568-578 (1999).

Wadwa et al., "Receptor mediated glycotargeting," *J. Drug Targeting*, 3, 111-127 (1995).

Wrighton et al., "Increased potency of an erythropoietin peptide mimetic through covalent dimerization," *Nature Biotechnology*, 15, 1261-1265 (1997).

Yang et al., *Cancer Research*, 69 (15), 6223-6231 (2009).

\* cited by examiner

SMOOTHENED POLYPEPTIDES AND METHODS OF USE

CROSS-REFERENCE TO RELATED APPLICATIONS

This patent application is a continuation of U.S. patent application Ser. No. 12/513,091, filed Aug. 11, 2009, now U.S. Pat. No. 8,198,402, which is a U.S. National Phase of International Patent Application No. PCT/US2007/83027, filed on Oct. 30, 2007, which claims the benefit of U.S. Provisional Patent Application No. 60/855,422, filed Oct. 31, 2006, each of which is incorporated by reference in its entirety herein.

INCORPORATION-BY-REFERENCE OF MATERIAL SUBMITTED ELECTRONICALLY

Incorporated by reference in its entirety herein is a computer-readable nucleotide/amino acid sequence listing submitted concurrently herewith and identified as follows: One 54,744 Byte ASCII (Text) file named "710429_ST25.txt" dated May 14, 2012.

BACKGROUND OF THE INVENTION

Cancer is caused by dysregulations of signal transduction pathways. One such pathway is the Hedgehog (HH) signal transduction pathway, which involves the Patch (Ptch) and Smoothened (SMO) proteins. The HH pathway is essential for embryonic cell growth (Beachy et al., *Nature*, 432: 324-331 (2004)) and was found to be dysregulated in several cancers, including breast cancer (Katano et al., *Cancer Lett.*, 227: 99-104 (2005)), prostate cancer (Sanchez et al., *Proc. Natl. Acad. Sci. U.S.A.*, 101: 12561-12566 (2004)), stomach cancer (Berman et al., *Nature*, 425: 846-851 (2003)), colon cancer (Douard et al., *Surgery*, 139: 665-670 (2006)), liver cancer (Sicklick et al., *Carcinogenesis*, 27: 748-757 (2006)), melanoma (Pons et al., *Clin. Transl. Oncol.*, 8: 466-474 (2006)), basal cell carcinoma (Lam et al., *Oncogene*, 18, 833-836 (1999)), and medulloblastoma (Berman et al., *Science*, 297, 1559-1561 (2002) and Romer et al., *Cancer Res.*, 65, 4975-4978 (2005)). There is a desire for inhibitors of the HH pathway for use in treatment of cancers.

BRIEF SUMMARY OF THE INVENTION

The invention provides an isolated or purified polypeptide or a peptidomimetic, as well as a fatty acid derivative thereof. The polypeptide or peptidomimetic comprises an amino acid sequence corresponding to a portion of a SMO protein, wherein the portion comprises an amino acid sequence of any of SEQ ID NOs: 2 to 4, each sequence of which generally corresponds to an intracellular loop of the SMO protein. The polypeptide or peptidomimetic can be a functional fragment of the portion, which functional fragment comprises at least 7 contiguous amino acids of SEQ ID NO: 2, 3, or 4. The polypeptide or peptidomimetic can be a functional variant of the portion or of the functional fragment. The inventive polypeptides and peptidomimetics (including fatty acid derivatives thereof, functional fragments and functional variants) inhibit the HH pathway and/or proliferation of a diseased cell.

The invention also provides conjugates comprising any of the inventive polypeptides or peptidomimetics, or fatty acid derivatives thereof. Further provided are nucleic acids encoding the inventive polypeptides, as well as related recombinant expression vectors and host cells. Pharmaceutical compositions comprising any of the inventive polypeptides, peptidomimetics, fatty acid derivatives, conjugates, nucleic acids, and recombinant expression vectors are furthermore provided by the invention.

The inventive pharmaceutical compositions are useful for inhibiting proliferation of a diseased cell, such that the invention moreover provides a method of inhibiting proliferation of a diseased cell. The method comprises contacting the diseased cell with an inventive pharmaceutical composition in an amount effective to inhibit proliferation of the diseased cell.

The invention provides other methods of use of the inventive pharmaceutical compositions, including a method of treating or preventing cancer in a host, a method of treating psoriasis in a host, a method of treating a neoplasm in a host, and a method of inhibiting expression of a gene selected from the group consisting of Gli-1, Gli-2, Gli-3, Ptch, Shh, Smo, and NES in a diseased cell.

DETAILED DESCRIPTION OF THE INVENTION

Figure 1:
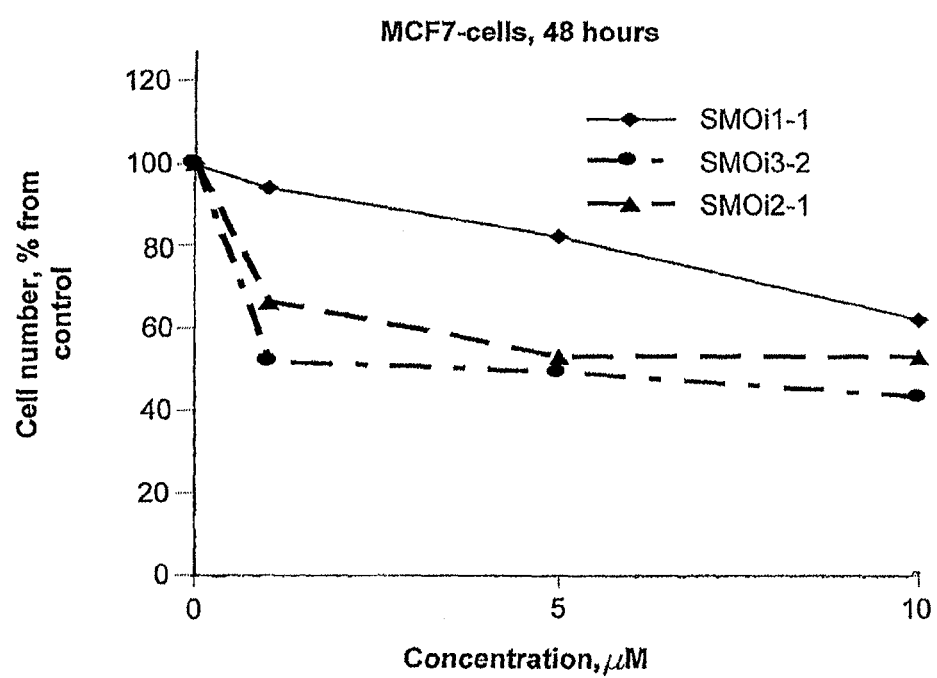
FIG. 1 depicts the % of viable MCF-7 breast cancer cells (relative to a control) upon a 48-hour treatment as a function of concentration of SMOi1-1, SMOi2-1, and SMOi3-1 lipidated polypeptides, in accordance with an embodiment of the invention.

SMO proteins are transmembrane proteins which function in the Hedgehog (HH) signal transduction pathway (see, for instance, Huangfu and Anderson, *Development* 133: 3-14 (2006)), which, as discussed is related to several cancers, e.g., breast cancer, prostate cancer, stomach cancer, etc. These proteins comprise an extracellular domain, seven transmembrane domains, three intracellular loops, and an intracellular domain. SMO proteins resemble a G-protein coupled receptor (GPCR) in general topology but appear to signal differently from the GPCRs. Examples of SMO proteins include human SMO proteins (e.g., GenBank Accession No. NP_005622 (SEQ ID NO: 1)), as well as orthologs thereof, such as mouse SMO proteins (e.g., GenBank Accession No. NP_795970), rat SMO proteins (e.g., GenBank Accession No. NP_036939), fruit fly SMO proteins (e.g., GenBank Accession No. NP_523443), zebra fish SMO proteins (e.g., GenBank Accession No. NP_571102), chicken SMO proteins, (e.g., GenBank Accession No. AAB84389), African clawed frog SMO proteins (e.g., GenBank Accession No. AAK15464).

The invention provides an isolated or purified polypeptide comprising an amino acid sequence corresponding to a portion of a SMO protein, wherein the portion comprises an amino acid sequence of any of SEQ ID NOs: 2 to 4, each of which is identical to or substantially identical to an intracellular loop of the SMO protein. For example, SEQ ID NO: 2 contains one additional amino acid (Leu) at the N-terminus of the second intracellular loop of SMO.

As used herein, the term "polypeptide" refers to a single chain of amino acids connected by one or more peptide bonds. In this regard, the term encompasses peptides, oligopeptides, and polypeptides of any length, provided that there is at least one peptide bond. For purposes herein, the polypeptide of the invention comprises at least 6 peptide bonds, e.g., 10 or more peptide bonds.

The inventive polypeptides comprise an amino acid sequence of a portion of a SMO protein. That is to say that the polypeptides of the invention do not encompass any full-length, wild-type SMO proteins, e.g., SEQ ID NO: 1. In this respect, the inventive polypeptides comprise less than about 780 amino acids of a wild-type SMO protein. For example, the inventive polypeptides comprise less than about 500 amino acids of a wild-type SMO protein. Most preferably, the inventive polypeptides comprise less than about 75, e.g., about 50, amino acids of a wild-type SMO protein. Also preferred is that the inventive polypeptides comprise about 10 to about 12 amino acids (excluding any CPP, as discussed herein).

The portion of the SMO protein, in accordance with an embodiment of the invention, comprises an amino acid sequence of any of SEQ ID NOs: 2 to 4. In this regard, the inventive polypeptides can comprise, consist essentially of, or consist of an amino acid sequence of SEQ ID NO: 2, 3, or 4.

Alternatively, the portion of the SMO protein comprises an amino acid sequence of any of SEQ ID NOs: 5 to 8. In this regard, the inventive polypeptides can comprise, consist essentially of, or consist of an amino acid sequence of SEQ ID NO: 5, 6, 7, or 8.

Included in the scope of the invention are functional fragments of the inventive polypeptides described herein. The term "functional fragment" when used in reference to an inventive polypeptide refers to any part or portion of the polypeptide of the invention, which part or portion retains the biological activity of the polypeptide of which it is a part (the parent polypeptide). The functional fragment can be any fragment comprising contiguous amino acids of the polypeptide of which it is a part, provided that the functional fragment inhibits proliferation of a diseased cell. Functional fragments encompass, for example, those parts of an inventive polypeptide that retain the ability to inhibit proliferation, or treat or prevent a disease (e.g., cancer, neoplasm, psoriasis), to a similar extent, the same extent, or to a higher extent, as the parent polypeptide. In reference to the parent polypeptide, the functional fragment can comprise, for instance, about 10%, 25%, 30%, 50%, 68%, 80%, 90%, 95%, or more, of the parent polypeptide.

The functional fragment can comprise additional amino acids at the amino or carboxy terminus, or at both termini, e.g., amino acids not found in the amino acid sequence of the parent polypeptide. Desirably, the additional amino acids do not interfere with the biological function of the functional fragment, e.g., inhibit proliferation, or treat or prevent a disease (e.g., cancer, neoplasm, psoriasis). More desirably, the additional amino acids enhance the biological activity, as compared to the biological activity of the parent polypeptide.

In a preferred embodiment of the invention, the functional fragment comprises at least 5 contiguous amino acids of SEQ ID NO: 2, 3, or 4 and inhibits proliferation of a diseased cell. In a more preferred embodiment of the invention, the functional fragment comprises at least 7 contiguous amino acids of SEQ ID NO: 2, 3, or 4. In a further preferred embodiment of the invention, the functional fragment comprises at least 4 contiguous amino acids of SEQ ID NO: 2, 3, or 4 and inhibits proliferation of a diseased cell. The functional fragment of the invention can, for example, comprise an amino acid sequence selected from the group consisting of SEQ ID NOs: 5 to 8. For instance, the functional fragment can comprise an amino acid sequence selected from the group consisting of SEQ ID NOs: 9 to 33. Also, the functional fragment of the invention can consist essentially of or consist of an amino acid sequence of any of SEQ ID NOs: 9 to 33.

Further included in the scope of the invention are functional variants of the inventive polypeptides, as well as functional variants of the inventive functional fragments described herein. The term "functional variant" as used herein refers to a polypeptide having substantial or significant sequence identity or similarity to a parent polypeptide or parent functional fragment, which functional variant retains the biological activity of the polypeptide or functional fragment of which it is a variant. Functional variants encompass, for example, those variants of the inventive polypeptide described herein (the parent polypeptide) and those variants of the functional fragment described herein (the parent functional fragment) that retain the ability to inhibit proliferation of a diseased cell to a similar extent, the same extent, or to a higher extent, as the parent polypeptide or parent functional fragment. In reference to the parent polypeptide or parent functional fragment, the functional variant can, for instance, be at least about 30%, 50%, 75%, 80%, 90%, 98% or more identical in amino acid sequence to the parent polypeptide or parent functional fragment.

The functional variant can, for example, comprise the amino acid sequence of the parent polypeptide or parent functional fragment with at least one conservative amino acid substitution. In this regard, the functional variant can comprise the amino acid sequence of the parent polypeptide or parent functional fragment with two, three, four, five, or more conservative amino acid substitutions. Alternatively or additionally, the functional variants can comprise the amino acid sequence of the parent polypeptide or parent functional fragment with at least one non-conservative amino acid substitution. In this regard, the functional variant can comprise the amino acid sequence of the parent polypeptide or parent functional fragment with two, three, four, five, or more non-conservative amino acid substitutions. In this case, it is preferable for the non-conservative amino acid substitution to not interfere with or inhibit the biological activity of the functional variant. Preferably, the non-conservative amino acid substitution enhances the biological activity of the functional variant, such that the biological activity of the functional variant is increased as compared to the parent polypeptide or parent functional fragment.

The functional variants preferably comprise one or more conservative amino acid substitutions. Conservative amino acid substitutions are known in the art, and include amino acid substitutions in which one amino acid having certain physical and/or chemical properties is exchanged for another amino acid that has the same chemical or physical properties. For instance, the conservative amino acid substitution can be an acidic amino acid substituted for another acidic amino acid (e.g., Asp or Glu), an amino acid with a nonpolar side chain substituted for another amino acid with a nonpolar side chain (e.g., Ala, Gly, Val, Ile, Leu, Met, Phe, Pro, Trp, Val, etc.), a basic amino acid substituted for another basic amino acid (Lys, Arg, etc.), an amino acid with a polar side chain substituted for another amino acid with a polar side chain (Asn, Cys, Gln, Ser, Thr, Tyr, etc.), an aromatic amino acid (Trp, Phe, Tyr, etc.) for another aromatic amino acid, etc.

Desirably, the functional variants of the invention comprise at least 4 contiguous amino acids of SEQ ID NO: 2, 3, or 4, have at least 75% sequence identity (e.g., 80%, 85%, 90%, 95% sequence identity) to the parent polypeptide or parent functional fragment, and inhibit proliferation of a diseased cell.

For example, the functional variant can be a functional variant of any of SEQ ID NOs: 17 to 21 and 23 to 33. In this regard, the functional variants can comprise the amino acid sequence of any of SEQ ID NOs: 38 to 54 and 57 to 59, wherein Xaa is selected from a group consisting of Tyr, Phe, or BPA.

Also, for example, the functional variant can be a functional variant of SMOi2-8 (SEQ ID NO: 23) comprising the amino acid sequence of SMOi2-8 with one of the amino acids at any of positions 1-7, 9, 11, and 12 is substituted with Ala.

Alternatively, the functional variant can comprise a retroinverso analogue of any of the inventive polypeptides or functional fragments described herein. The term "retroinverso analogue" refers to a polypeptide comprising a reversed amino acid sequence of a parent polypeptide, such that the amino acid sequence of the retroinverso analogue (when read from the N-terminus to the C-terminus) is the same as the amino acid sequence of the parent polypeptide when read from the C-terminus to the N-terminus. Furthermore, with respect to a retroinverso analogue, each of the amino acids is the D isomer of the amino acid, as opposed to the L isomer. For example, the retroinverso analogue of the tripeptide Val-Ala-Gly has an amino acid sequence Gly-Ala-Val, in which each amino acid is the D isomer. With respect to the invention, the functional variant preferably comprises a retroinverso analogue of SEQ ID NO: 23, 26, or 33. In this regard, the functional variant comprises the amino acid sequence of any of SEQ ID NOs: 34 to 37.

The polypeptides of the invention (including functional fragments and functional variants) can be obtained by methods known in the art. Suitable methods of de novo synthesizing polypeptides are described in references, such as Chan et al., *Fmoc Solid Phase Peptide Synthesis*, Oxford University Press, Oxford, United Kingdom, 2005; *Peptide and Protein Drug Analysis*, ed. Reid, R., Marcel Dekker, Inc., 2000; *Epitope Mapping*, ed. Westwoood et al., Oxford University Press, Oxford, United Kingdom, 2000; and U.S. Pat. No. 5,449,752. Also, polypeptides can be recombinantly produced using the nucleic acids described herein using standard recombinant methods. See, for instance, Sambrook et al., *Molecular Cloning: A Laboratory Manual*, 3$^{rd}$ ed., Cold Spring Harbor Press, Cold Spring Harbor, N.Y. 2001; and Ausubel et al., *Current Protocols in Molecular Biology*, Greene Publishing Associates and John Wiley & Sons, NY, 1994. Further, some of the polypeptides of the invention (including functional fragments and functional variants thereof) can be isolated and/or purified from a source, such as a plant, a bacterium, an insect, a mammal, e.g., a rat, a human, etc. Methods of isolation and purification are well-known in the art. Alternatively, the polypeptides described herein (including functional fragments and functional variants thereof) can be synthesized or obtained commercially from companies such as Synpep (Dublin, Calif.), Peptide Technologies Corp. (Gaithersburg, Md.), and Multiple Peptide Systems (San Diego, Calif.). In this respect, the inventive polypeptides can be synthetic, recombinant, isolated, and/or purified.

Also provided by the invention are peptidomimetics of any of the inventive polypeptides (including functional fragments and functional variants) described herein. The term "peptidomimetic" as used herein refers to a compound which has essentially the same general structure of a corresponding polypeptide with modifications that increase its stability or biological function. A peptidomimetic includes, for example, those compounds comprising the same amino acid sequence of a corresponding polypeptide with an altered backbone between two or more of the amino acids. Additionally, the peptidomimetic can comprise synthetic or non-naturally occurring amino acids in place of naturally-occurring amino acids.

In a preferred embodiment, the peptidomimetic is a peptoid. The term "peptoid" as used herein refers to a peptidomimetic in which the sidechains of each amino acid is appended to the nitrogen atom of the amino acid as opposed to the alpha carbon. For example, peptoids can be considered as N-substituted glycines which have repeating units of the general structure of NRCH$_2$CO and which have the same or substantially the same amino acid sequence as the corresponding polypeptide.

In another preferred embodiment, the peptidomimetic comprises an altered backbone in which the bond between each amino acid is methylated. In this regard, the peptidomimetic can comprise a methylated peptide backbone of the following structure:

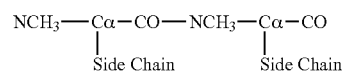

The polypeptides (including functional fragments and functional variants) and peptidomimetics of the invention can be of any length, i.e., can comprise any number of amino acids, provided that the polypeptide (or functional fragment or functional variant thereof) or peptidomimetic retains their biological activity, e.g., the ability to inhibit proliferation of a diseased cell, treat or prevent disease (e.g., cancer, neoplasm, psoriasis) in a host, etc. For example, the inventive polypeptide or peptidomimetic can be 50 to 5000 amino acids long, such as 5, 6, 7, 8, 9, 10, 11, 12, 13, 14, 15, 16, 20, 25, 30, 40, 50, 70, 75, 100, 125, 150, 175, 200, 300, 400, 500, 600, 700, 800, 900, 1000 or more amino acids in length. Preferably, the polypeptides of the invention are 5 to 50 amino acids in length.

The polypeptides (including functional fragments and functional variants) and peptidomimetics of the invention can comprise synthetic amino acids in place of one or more naturally-occurring amino acids. Such synthetic amino acids are known in the art, and include, for example, aminocyclohexane carboxylic acid, norleucine, α-amino n-decanoic acid, homoserine, S-acetylaminomethyl-cysteine, trans-3- and trans-4-hydroxyproline, 4-aminophenylalanine, 4-benzoylphenylalanine, 4-nitrophenylalanine, 4-chlorophenylalanine, 4-carboxyphenylalanine, β-phenylserine, β-hydroxyphenylalanine, phenylglycine, α-naphthylalanine, cyclohexylalanine, cyclohexylglycine, indoline-2-carboxylic acid, 1,2,3,4-tetrahydroisoquinoline-3-carboxylic acid, aminomalonic acid, aminomalonic acid monoamide, N'-benzyl-N'-methyl-lysine, N',N'-dibenzyl-lysine, 6-hydroxylysine, ornithine, α-aminocyclopentane carboxylic acid, α-aminocyclohexane carboxylic acid, α-aminocycloheptane carboxylic acid, α-(2-amino-2-norbornane)-carboxylic acid, α,γ-diaminobutyric acid, α,β-diaminopropionic acid, homophenylalanine, and α-tert-butylglycine.

The polypeptides (including functional fragments and functional variants) and peptidomimetics of the invention can be lipidated (e.g., fatty acidated), glycosylated, amidated, carboxylated, phosphorylated, esterified, N-acylated, cyclized via, e.g., a disulfide bridge, or converted into an acid addition salt and/or optionally dimerized or polymerized, or conjugated.

In this regard, the invention further provides lipidated derivatives of any of the polypeptides (including functional fragments and functional variants) and peptidomimetics of the invention. Lipidated derivatives of the invention encompass any of the polypeptides and peptidomimetics described herein comprising a lipid molecule. As used herein, the term "lipid molecule" refers to any molecule comprising a hydrophobic moiety which facilitates the entry of the polypeptide (including functional fragments and functional variants) or peptidomimetic across the cell membrane and into the cell. The lipid can be any lipid known in the art, such as, for example, a fatty acid, a farnesyl group (e.g., farnesyl diphosphate), a geranylgeranyl group (e.g., geranylgeranyl diphosphate), a phospholipid group, glycophosphatidylinositol, phosphatidylserine, phosphatidylethanolamine, sphingomyelin, phosphatidylcholine, cardiolipin, phosphatidylinositol, phosphatidic acid, lysophosphoglyceride, and a cholesterol group.

Preferably, the lipidated derivative is a fatty acid derivative in which the polypeptide or peptidomimetic described herein comprises a fatty acid molecule. The fatty acid molecule can be any $C_8$ to $C_{20}$ fatty acid. The fatty acid molecule can be, e.g., lauric acid, palmitic acid, myristic acid, stearic acid, oleic acid, linoleic acid, α-linoleic acid, linolenic acid, arachidonic acid, timnodonic acid, docosohexenoic acid, erucic acid, arachidic acid, or behenic acid. The fatty acid may optionally contain additional functional groups, e.g., one or more amino groups on any of the carbon atoms. In a preferred embodiment, the fatty acid molecule is a $C_8$ to $C_{16}$ fatty acid, for example, a $C_{16}$ fatty acid. In a more preferred embodiment, the fatty acid is palmitate.

As is true with respect to the lipid molecule, the fatty acid molecule can be attached to any suitable part of the inventive polypeptide (including functional fragment and functional variant) or peptidomimetic. In a preferred embodiment of the invention, the fatty acid derivative of the inventive polypeptide (including functional fragment and functional variant) or peptidomimetic comprises a fatty acid molecule at the amino (N-) terminus, the carboxyl (C-) terminus, or both the N- and C-termini.

The fatty acid molecule can be attached to the inventive polypeptide (including functional fragment and functional variant) or peptidomimetic directly or through a linker. In an embodiment of the invention, when the fatty acid molecule is at the C-terminus of the inventive polypeptide or peptidomimetic, the fatty acid molecule is attached through an amino acid linker selected from the group consisting of Lys, Cys, homocysteine (homoCys), Orn, α,γ-diaminobutyric acid, and α,β-diaminopropionic acid. In a preferred embodiment of the invention, the fatty acid molecule is attached through a Lys. In a more preferred embodiment of the invention, the fatty acid molecule is attached through the epsilon carbon of Lys.

In another preferred embodiment, when the fatty acid molecule is at the C-terminus of the inventive polypeptide or peptidomimetic, the fatty acid molecule is modified e.g., to include an amino group such as in a modified molecule of Formula I or Formula II, wherein Formula I is $NH_2(CH_2)_nCOOH$ and Formula II is $CH_3(CH_2)_mCH(NH_2)COOH$, wherein each of n and m is 1 to 24. In this regard, the fatty acid molecule is attached to the carboxyl group of the C-terminal amino acid of the polypeptide or peptidomimetic. Preferably, n or m is 8 to 16. More preferably, n or m is 16.

Alternatively, the inventive polypeptides (including functional fragments and functional variants) or peptidomimetics described herein can comprise a cell-penetrating peptide (CPP). Such a CPP facilitates the entry of the inventive polypeptide or peptidomimetic across the cell membrane and into the cell. CPPs are known in the art. See, for example, Deshayes et al., *Cell. Mol. Life. Sci.* 62: 1839-1849 (2005); El-Andaloussi et al., *Curr. Pharm. Design* 11: 3597-3611 (2005); and Mae and Langel, *Curr. Opin. Pharmacol.* 6: 509-514 (2006)). The CPP can be any of those known in the art, e.g., Transportan, VP22, Pep1, and the like. Preferably, the CPP comprises an amino acid sequence of SEQ ID NO: 78 or 79, which corresponds to the amino acid sequence of penetratin and Tat (48-60), respectively.

The polypeptides (including functional fragments and functional variants) and peptidomimetics, including fatty acid derivatives thereof, of the invention can be a monomer peptide, or can be a dimer or multimer peptide. For example, the polypeptide can be a dimer of the following general structure:

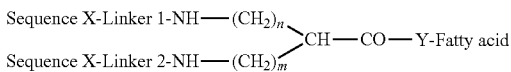

wherein Sequence X is selected from the group consisting of Ac-LAKFSTHWAYTL (all-D) (SEQ ID NO: 85); Ac-AKFSTHWAYTL (All-D) (SEQ ID NO: 86); and Ac-KFSTHWAYTL (All-D) (SEQ ID NO: 87); wherein each of Linker 1 and Linker 2 is optionally present and each independently is Gly, beta-Ala, aminopropionic acid, gamma-aminobutyric acid, aminocaproic acid, or aminohexanoic acid; wherein n and m is between 0 and 6; wherein Y is K, C, homoCys, Orn, diaminopropanoic acid (DPA), diaminobutyric acid (DBA); and wherein the fatty acid is a stearic, palmitic, myristic, lauric, capric or caprilic acid. In a preferred embodiment, Sequence X is SEQ ID NO: 87, n is 4, m is 0, each of Linker 1 and Linker 2 is beta-Ala, and the fatty acid is palmitate. Methods of making dimeric and multimeric polypeptides are known in the art. See, for example, Wrighton et al., *Nature Biotechnology* 15: 1261-1265 (1997). A preferred method of making a dimeric polypeptide also is set forth herein as Example 1.

When the polypeptides (including functional fragments and functional variants) and peptidomimetics, including fatty acid derivatives thereof, of the invention are in the form of a salt, preferably, the polypeptides or peptidomimetcs are in the form of a pharmaceutically acceptable salt. Suitable pharmaceutically acceptable acid addition salts include those derived from mineral acids, such as hydrochloric, hydrobromic, phosphoric, metaphosphoric, nitric, and sulphuric acids, and organic acids, such as tartaric, acetic, citric, malic, lactic, fumaric, benzoic, glycolic, gluconic, succinic, and arylsulphonic acids, for example, p-toluenesulphonic acid.

Further provided by the invention is a nucleic acid encoding any of the inventive polypeptides, including functional fragments and functional variants, described herein. As used herein, the term "nucleic acid" encompasses "polynucleotide," "oligonucleotide," and "nucleic acid molecule," and generally refers to a polymer of DNA or RNA, which can be single-stranded or double-stranded, synthesized or obtained (e.g., isolated and/or purified) from natural sources, which can contain natural, non-natural or altered nucleotides, and which can contain a natural, non-natural or altered internucleotide linkage, such as a phosphoroamidate linkage or a phosphorothioate linkage, instead of the phosphodiester found between the nucleotides of an unmodified oligonucleotide. It is generally preferred that the nucleic acid does not comprise any insertions, deletions, inversions, and/or substitutions. However, it may be suitable in some instances, as discussed herein, for the nucleic acid to comprise one or more insertions, deletions, inversions, and/or substitutions.

Preferably, the nucleic acids of the invention are recombinant. As used herein, the term "recombinant" refers to (i) molecules that are constructed outside living cells by joining natural or synthetic nucleic acid segments to nucleic acid molecules that can replicate in a living cell, or (ii) molecules that result from the replication of those described in (i) above. For purposes herein, the replication can be in vitro replication or in vivo replication.

The nucleic acids can be constructed based on chemical synthesis and/or enzymatic ligation reactions using procedures known in the art. See, for example, Sambrook et al., supra, and Ausubel et al., supra. For example, a nucleic acid can be chemically synthesized using naturally occurring nucleotides or variously modified nucleotides designed to increase the biological stability of the molecules or to increase the physical stability of the duplex formed upon hybridization (e.g., phosphorothioate derivatives and acridine substituted nucleotides). Examples of modified nucleotides that can be used to generate the nucleic acids include, but are not limited to, 5-fluorouracil, 5-bromouracil, 5-chlorouracil, 5-iodouracil, hypoxanthine, xanthine, 4-acetylcytosine, 5-(carboxyhydroxymethyl) uracil, 5-carboxymethylaminomethyl-2-thiouridine, 5-carboxymethylaminomethyluracil, dihydrouracil, beta-D-galactosylqueosine, inosine, $N^6$-isopentenyladenine, 1-methylguanine, 1-methylinosine, 2,2-dimethylguanine, 2-methyladenine, 2-methylguanine, 3-methylcytosine, 5-methylcytosine, $N^6$-substituted adenine, 7-methylguanine, 5-methylaminomethyluracil, 5-methoxyaminomethyl-2-thiouracil, beta-D-mannosylqueosine, 5'-methoxycarboxymethyluracil, 5-methoxyuracil, 2-methylthio-$N^6$-isopentenyladenine, uracil-5-oxyacetic acid (v), wybutoxosine, pseudouracil, queosine, 2-thiocytosine, 5-methyl-2-thiouracil, 2-thiouracil, 4-thiouracil, 5-methyluracil, uracil-5-oxyacetic acid methylester, 3-(3-amino-3-N-2-carboxypropyl) uracil, and 2,6-diaminopurine. Alternatively, one or more of the nucleic acids of the invention can be purchased from companies, such as Macromolecular Resources (Fort Collins, Colo.) and Synthegen (Houston, Tex.).

The nucleic acid can comprise any nucleotide sequence which encodes any of the inventive polypeptides, including functional fragments and functional variants. For example, the nucleic acid can comprise a nucleotide sequence encoding any of SEQ ID NOs: 2 to 29, 32, 33, 38 to 48, 53 to 56, 59 to 66, 70 to 72, 76, and 80. The nucleic acid alternatively can comprise a nucleotide sequence which is degenerate to any of these sequences or a combination of degenerate sequences. The invention also provides an isolated or purified nucleic acid comprising a nucleotide sequence which is complementary to the nucleotide sequence of any of the nucleic acids described herein or a nucleotide sequence which hybridizes under stringent conditions to the nucleotide sequence of any of the nucleic acids described herein.

The nucleic acids of the invention can be incorporated into a recombinant expression vector. In this regard, the invention provides recombinant expression vectors comprising any of the nucleic acids of the invention. For purposes herein, the term "recombinant expression vector" means a genetically-modified oligonucleotide or polynucleotide construct that permits the expression of an mRNA, protein, polypeptide, or peptide by a host cell, when the construct comprises a nucleotide sequence encoding the mRNA, protein, polypeptide, or peptide, and the vector is contacted with the cell under conditions sufficient to have the mRNA, protein, polypeptide, or peptide expressed within the cell. The vectors of the invention are not naturally-occurring as a whole. However, parts of the vectors can be naturally-occurring. The inventive recombinant expression vectors can comprise any type of nucleotides, including, but not limited to DNA and RNA, which can be single-stranded or double-stranded, synthesized or obtained in part from natural sources, and which can contain natural, non-natural or altered nucleotides. The recombinant expression vectors can comprise naturally-occurring, non-naturally-occurring internucleotide linkages, or both types of linkages. Preferably, the non-naturally occurring or altered nucleotides or internucleotide linkages does not hinder the transcription or replication of the vector.

The recombinant expression vector of the invention can be any suitable recombinant expression vector, and can be used to transform or transfect any suitable host. Suitable vectors include those designed for propagation and expansion or for expression or both, such as plasmids and viruses. The vector can be selected from the group consisting of the pUC series (Fermentas Life Sciences), the pBluescript series (Stratagene, LaJolla, Calif.), the pET series (Novagen, Madison, Wis.), the pGEX series (Pharmacia Biotech, Uppsala, Sweden), and the pEX series (Clontech, Palo Alto, Calif.). Bacteriophage vectors, such as λGT10, λGT11, λZapII (Stratagene), λEMBL4, and λNM1149, also can be used. Examples of plant expression vectors include pBI01, pBI101.2, pBI101.3, pBI121 and pBIN19 (Clontech). Examples of animal expression vectors include pEUK-Cl, pMAM and pMAMneo (Clontech). Preferably, the recombinant expression vector is a viral vector, e.g., a retroviral vector.

The recombinant expression vectors of the invention can be prepared using standard recombinant DNA techniques described in, for example, Sambrook et al., supra, and Ausubel et al., supra. Constructs of expression vectors, which are circular or linear, can be prepared to contain a replication system functional in a prokaryotic or eukaryotic host cell. Replication systems can be derived, e.g., from ColE1, 2μ plasmid, λ, SV40, bovine papilloma virus, and the like.

Desirably, the recombinant expression vector comprises regulatory sequences, such as transcription and translation initiation and termination codons, which are specific to the type of host (e.g., bacterium, fungus, plant, or animal) into which the vector is to be introduced, as appropriate and taking into consideration whether the vector is DNA- or RNA-based.

The recombinant expression vector can include one or more marker genes, which allow for selection of transformed or transfected hosts. Marker genes include biocide resistance, e.g., resistance to antibiotics, heavy metals, etc., complementation in an auxotrophic host to provide prototrophy, and the like. Suitable marker genes for the inventive expression vectors include, for instance, neomycin/G418 resistance genes, hygromycin resistance genes, histidinol resistance genes, tetracycline resistance genes, and ampicillin resistance genes.

The recombinant expression vector can comprise a native or normative promoter operably linked to the nucleotide sequence encoding the modified TCR, polypeptide, or protein (including functional portions and functional variants thereof), or to the nucleotide sequence which is complementary to or which hybridizes to the nucleotide sequence encoding the modified TCR, polypeptide, or protein. The selection of promoters, e.g., strong, weak, inducible, tissue-specific and developmental-specific, is within the ordinary skill of the artisan. Similarly, the combining of a nucleotide sequence with a promoter is also within the skill of the artisan. The promoter can be a non-viral promoter or a viral promoter, e.g., a cytomegalovirus (CMV) promoter, an SV40 promoter, an RSV promoter, and a promoter found in the long-terminal repeat of the murine stem cell virus.

The inventive recombinant expression vectors can be designed for either transient expression, for stable expression, or for both. Also, the recombinant expression vectors can be made for constitutive expression or for inducible expression.

Further, the recombinant expression vectors can be made to include a suicide gene. As used herein, the term "suicide gene" refers to a gene that causes the cell expressing the suicide gene to die. The suicide gene can be a gene that confers sensitivity to an agent, e.g., a drug, upon the cell in which the gene is expressed, and causes the cell to die when the cell is contacted with or exposed to the agent. Suicide genes are known in the art (see, for example, *Suicide Gene Therapy: Methods and Reviews*, Springer, Caroline J. (Cancer Research UK Centre for Cancer Therapeutics at the Institute of Cancer Research, Sutton, Surrey, UK), Humana Press, 2004) and include, for example, the Herpes Simplex Virus (HSV) thymidine kinase (TK) gene, cytosine daminase, purine nucleoside phosphorylase, and nitroreductase.

The invention further provides a host cell comprising any of the recombinant expression vectors described herein. As used herein, the term "host cell" refers to any type of cell that can contain the inventive recombinant expression vector. The host cell can be a eukaryotic cell, e.g., plant, animal, fungi, or algae, or can be a prokaryotic cell, e.g., bacteria or protozoa. The host cell can be a cultured cell or a primary cell, i.e., isolated directly from an organism, e.g., a human. The host cell can be an adherent cell or a suspended cell, i.e., a cell that grows in suspension. Suitable host cells are known in the art and include, for instance, DH5α *E. coli* cells, Chinese hamster ovarian cells, monkey VERO cells, COS cells, HEK293 cells, and the like. For purposes of amplifying or replicating the recombinant expression vector, the host cell is preferably a prokaryotic cell, e.g., a DH5α cell. For purposes of producing a recombinant modified TCR, polypeptide, or protein, the host cell is preferably a mammalian cell. Most preferably, the host cell is a human cell. The host cell can be of any cell type, can originate from any type of tissue, and can be of any developmental stage.

Also provided by the invention is a population of cells comprising at least one host cell described herein. The population of cells can be a heterogeneous population comprising the host cell comprising any of the recombinant expression vectors described, in addition to at least one other cell, e.g., a host cell (e.g., a T cell), which does not comprise any of the recombinant expression vectors, or a cell other than a T cell, e.g., a B cell, a macrophage, a neutrophil, an erythrocyte, a hepatocyte, an endothelial cell, an epithelial cells, a muscle cell, a brain cell, etc. Alternatively, the population of cells can be a substantially homogeneous population, in which the population comprises mainly of host cells (e.g., consisting essentially of) comprising the recombinant expression vector. The population also can be a clonal population of cells, in which all cells of the population are clones of a single host cell comprising a recombinant expression vector, such that all cells of the population comprise the recombinant expression vector. In one embodiment of the invention, the population of cells is a clonal population comprising host cells comprising a recombinant expression vector as described herein.

Included in the scope of the invention are conjugates, e.g., bioconjugates, comprising any of the inventive polypeptides (including any of the functional fragments or functional variants) or peptidomimetics, nucleic acids, recombinant expression vectors, or host cells. Conjugates, as well as methods of synthesizing conjugates in general, are known in the art (See, for instance, Hudecz, F., *Methods Mol. Biol.* 298: 209-223 (2005) and Kirin et al., *Inorg Chem.* 44(15): 5405-5415 (2005)).

The inventive polypeptides (including functional fragments and functional variants), peptidomimetics, fatty acid derivatives, nucleic acids, recombinant expression vectors, and host cells (including populations thereof) can be isolated, purified, synthetic, and/or recombinant. The term "isolated" as used herein means having been removed from its natural environment. The "purified" as used herein means having been increased in purity, wherein "purity" is a relative term, and not to be necessarily construed as absolute purity. For example, the purity can be at least about 50%, can be greater than 60%, 70%, 80%, or 90%, or can be 100%.

The inventive polypeptides (including functional fragments and functional variants), peptidomimetics, fatty acid derivatives, conjugates, nucleic acids, recombinant expression vectors, and host cells (including populations thereof), all of which are collectively referred to as "inventive materials" hereinafter, can be formulated into a composition, such as a pharmaceutical composition. In this regard, the invention provides a pharmaceutical composition comprising any of the polypeptides (including functional fragments and functional variants), peptidomimetics, fatty acid derivatives, conjugates, nucleic acids, recombinant expression vectors, and host cells (including populations thereof), and a pharmaceutically acceptable carrier. The inventive pharmaceutical compositions containing any of the inventive materials can comprise more than one inventive material, e.g., a polypeptide and a nucleic acid, or two or more different polypeptides. Alternatively, the pharmaceutical composition can comprise an inventive material in combination with another pharmaceutically active agent or drug, such as a chemotherapeutic agent, e.g., asparaginase, busulfan, carboplatin, cisplatin, daunorubicin, doxorubicin, fluorouracil, gemcitabine, hydroxyurea, methotrexate, paclitaxel, rituximab, vinblastine, vincristine, etc.

In a preferred embodiment of the invention, the pharmaceutical composition comprises the inventive material in combination with a lipid. The lipid can be any lipid, including, for example, a fatty acid, a phospholipid, a sterol, a sphingolipid, a terpene, a glycerolipid, a glycerophospholipid, a prenol lipid, a saccharolipid, and a polyketide. Such lipids are known in the art. See, for example, Fahy et al., *J. Lipid Res.* 46: 839-861 (2005). Preferably, the lipid is a cholesterol.

With respect to pharmaceutical compositions, the pharmaceutically acceptable carrier can be any of those conventionally used and is limited only by chemico-physical considerations, such as solubility and lack of reactivity with the active compound(s), and by the route of administration. The pharmaceutically acceptable carriers described herein, for example, vehicles, adjuvants, excipients, and diluents, are well-known to those skilled in the art and are readily available to the public. It is preferred that the pharmaceutically acceptable carrier be one which is chemically inert to the active agent(s) and one which has no detrimental side effects or toxicity under the conditions of use.

The choice of carrier will be determined in part by the particular inventive material, as well as by the particular method used to administer the inventive material. Accordingly, there are a variety of suitable formulations of the pharmaceutical composition of the invention. The following formulations for oral, aerosol, parenteral, subcutaneous, intravenous, intramuscular, intraarterial, intrathecal, interperitoneal, rectal, and vaginal administration are exemplary and are in no way limiting. More than one route can be used to administer the inventive materials, and in certain instances, a particular route can provide a more immediate and more effective response than another route. In a preferred embodiment of the invention, the pharmaceutical composition is a topical formulation, an intravenous formulation, or a subcutaneous formulation.

In a preferred embodiment of the invention, the pharmaceutical composition is a topical formulation. Topical formulations are well-known to those of skill in the art. Such formulations are particularly suitable in the context of the invention for application to the skin. The topical formulation of the invention can be, for instance, a cream, a lotion, an ointment, a patch, an oil, a paste, a spray, e.g., an aerosol spray, a gel, a mousse, a roll-on liquid, a solid stick, etc. Preferably, the topical formulation of the invention is a cream, a lotion, an ointment, or a patch. When the topical formulation is a lotion, preferably, the lotion also includes an ultraviolet (UV) light blocking agent, such as tocopheryl, aminobenzoic acid, Avobenzone, Cinoxate, dioxybenzone, homosalate, menthyl anthranilate, octocrylene, octyl methoxycinnamate, octisalate, oxybenzone, padimate O, phenylbenzimidazole, sulfonic acid, sulisobenzone, titanium dioxide, trolamine salicylate, and zinc oxide.

Formulations suitable for oral administration can consist of (a) liquid solutions, such as an effective amount of the inventive material dissolved in diluents, such as water, saline, or orange juice; (b) capsules, sachets, tablets, lozenges, and troches, each containing a predetermined amount of the active ingredient, as solids or granules; (c) powders; (d) suspensions in an appropriate liquid; and (e) suitable emulsions. Liquid formulations may include diluents, such as water and alcohols, for example, ethanol, benzyl alcohol, and the polyethylene alcohols, either with or without the addition of a pharmaceutically acceptable surfactant. Capsule forms can be of the ordinary hard- or soft-shelled gelatin type containing, for example, surfactants, lubricants, and inert fillers, such as lactose, sucrose, calcium phosphate, and corn starch. Tablet forms can include one or more of lactose, sucrose, mannitol, corn starch, potato starch, alginic acid, microcrystalline cellulose, acacia, gelatin, guar gum, colloidal silicon dioxide, croscarmellose sodium, talc, magnesium stearate, calcium stearate, zinc stearate, stearic acid, and other excipients, colorants, diluents, buffering agents, disintegrating agents, moistening agents, preservatives, flavoring agents, and other pharmacologically compatible excipients. Lozenge forms can comprise the inventive material in a flavor, usually sucrose and acacia or tragacanth, as well as pastilles comprising the inventive material in an inert base, such as gelatin and glycerin, or sucrose and acacia, emulsions, gels, and the like containing, in addition to, such excipients as are known in the art.

The inventive material, alone or in combination with other suitable components, can be made into aerosol formulations to be administered via inhalation. These aerosol formulations can be placed into pressurized acceptable propellants, such as dichlorodifluoromethane, propane, nitrogen, and the like. They also may be formulated as pharmaceuticals for non-pressured preparations, such as in a nebulizer or an atomizer. Such spray formulations also may be used to spray mucosa.

Formulations suitable for parenteral administration include aqueous and non-aqueous, isotonic sterile injection solutions, which can contain anti-oxidants, buffers, bacteriostats, and solutes that render the formulation isotonic with the blood of the intended recipient, and aqueous and non-aqueous sterile suspensions that can include suspending agents, solubilizers, thickening agents, stabilizers, and preservatives. The inventive material can be administered in a physiologically acceptable diluent in a pharmaceutical carrier, such as a sterile liquid or mixture of liquids, including water, saline, aqueous dextrose and related sugar solutions, an alcohol, such as ethanol or hexadecyl alcohol, a glycol, such as propylene glycol or polyethylene glycol, dimethylsulfoxide, glycerol, ketals such as 2,2-dimethyl-1,3-dioxolane-4-methanol, ethers, poly(ethyleneglycol) 400, oils, fatty acids, fatty acid esters or glycerides, or acetylated fatty acid glycerides with or without the addition of a pharmaceutically acceptable surfactant, such as a soap or a detergent, suspending agent, such as pectin, carbomers, methylcellulose, hydroxypropylmethylcellulose, or carboxymethylcellulose, or emulsifying agents and other pharmaceutical adjuvants.

Oils, which can be used in parenteral formulations include petroleum, animal, vegetable, or synthetic oils. Specific examples of oils include peanut, soybean, sesame, cottonseed, corn, olive, petrolatum, and mineral. Suitable fatty acids for use in parenteral formulations include oleic acid, stearic acid, and isostearic acid. Ethyl oleate and isopropyl myristate are examples of suitable fatty acid esters.

Suitable soaps for use in parenteral formulations include fatty alkali metal, ammonium, and triethanolamine salts, and suitable detergents include (a) cationic detergents such as, for example, dimethyl dialkyl ammonium halides, and alkyl pyridinium halides, (b) anionic detergents such as, for example, alkyl, aryl, and olefin sulfonates, alkyl, olefin, ether, and monoglyceride sulfates, and sulfosuccinates, (c) nonionic detergents such as, for example, fatty amine oxides, fatty acid alkanolamides, and polyoxyethylenepolypropylene copolymers, (d) amphoteric detergents such as, for example, alkyl-β-aminopropionates, and 2-alkyl-imidazoline quaternary ammonium salts, and (e) mixtures thereof.

The parenteral formulations will typically contain from about 0.5% to about 25% by weight of the inventive material in solution. Preservatives and buffers may be used. In order to minimize or eliminate irritation at the site of injection, such compositions may contain one or more nonionic surfactants having a hydrophile-lipophile balance (HLB) of from about 12 to about 17. The quantity of surfactant in such formulations will typically range from about 5% to about 15% by weight. Suitable surfactants include polyethylene glycol sorbitan fatty acid esters, such as sorbitan monooleate and the high molecular weight adducts of ethylene oxide with a hydrophobic base, formed by the condensation of propylene oxide with propylene glycol. The parenteral formulations can be presented in unit-dose or multi-dose sealed containers, such as ampoules and vials, and can be stored in a freeze-dried (lyophilized) condition requiring only the addition of the sterile liquid excipient, for example, water, for injections, immediately prior to use. Extemporaneous injection solutions and suspensions can be prepared from sterile powders, granules, and tablets of the kind previously described.

Injectable formulations are in accordance with the invention. The requirements for effective pharmaceutical carriers for injectable compositions are well-known to those of ordinary skill in the art (see, e.g., *Pharmaceutics and Pharmacy Practice*, J.B. Lippincott Company, Philadelphia, Pa., Banker and Chalmers, eds., pages 238-250 (1982), and *ASHP Handbook on Injectable Drugs*, Toissel, 4th ed., pages 622-630 (1986)). Preferably, when administering cells, e.g., dendritic cells, the cells are administered via injection.

Additionally, the inventive materials, or compositions comprising such inventive materials, can be made into suppositories by mixing with a variety of bases, such as emulsifying bases or water-soluble bases. Formulations suitable for vaginal administration can be presented as pessaries, tampons, creams, gels, pastes, foams, or spray formulas containing, in addition to the active ingredient, such carriers as are known in the art to be appropriate.

It will be appreciated by one of skill in the art that, in addition to the above-described pharmaceutical compositions, the inventive materials of the invention can be formulated as inclusion complexes, such as cyclodextrin inclusion complexes, or liposomes.

For purposes of the invention, the amount or dose of the inventive material administered should be sufficient to effect, e.g., a therapeutic or prophylactic response, in the subject or animal over a reasonable time frame. For example, the dose of the inventive material should be sufficient to inhibit proliferation of a diseased cell, or treat or prevent a disease (e.g., cancer, neoplasm, or psoriasis in a period of from about 2 hours or longer, e.g., 12 to 24 or more hours, from the time of administration. In certain embodiments, the time period could be even longer. The dose will be determined by the efficacy of the particular inventive material and the condition of the animal (e.g., human), as well as the body weight of the animal (e.g., human) to be treated.

Many assays for determining an administered dose are known in the art. For purposes of the invention, an assay, which comprises comparing the extent to which diseased cells are inhibited from proliferating, upon administration of a given dose of an inventive material to a mammal among a set of mammals of which is each given a different dose of the inventive material, could be used to determine a starting dose to be administered to a mammal. The extent to which diseased cells are inhibited from proliferating upon administration of a certain dose can be assayed by methods known in the art, including, for instance, the methods described herein as Example 2.

The dose of the inventive material also will be determined by the existence, nature and extent of any adverse side effects that might accompany the administration of a particular inventive material. Typically, the attending physician will decide the dosage of the inventive material with which to treat each individual patient, taking into consideration a variety of factors, such as age, body weight, general health, diet, sex, inventive material to be administered, route of administration, and the severity of the condition being treated. By way of example and not intending to limit the invention, the dose of the inventive material can be about 0.001 to about 1000 mg/kg body weight of the subject being treated/day, from about 0.01 to about 10 mg/kg body weight/day, about 0.01 mg to about 1 mg/kg body weight/day.

One of ordinary skill in the art will readily appreciate that the inventive materials of the invention can be modified in any number of ways, such that the therapeutic or prophylactic efficacy of the inventive materials is increased through the modification. For instance, the inventive materials can be conjugated either directly or indirectly through a linker to a targeting moiety. The practice of conjugating compounds, e.g., inventive materials, to targeting moieties is known in the art. See, for instance, Wadwa et al., J. *Drug Targeting* 3: 111 (1995) and U.S. Pat. No. 5,087,616. The term "targeting moiety" as used herein, refers to any molecule or agent that specifically recognizes and binds to a cell-surface receptor, such that the targeting moiety directs the delivery of the inventive materials to a population of cells on which surface the receptor is expressed. Targeting moieties include, but are not limited to, antibodies, or fragments thereof, peptides, hormones, growth factors, cytokines, and any other natural or non-natural ligands, which bind to cell surface receptors (e.g., Epithelial Growth Factor Receptor (EGFR), T-cell receptor (TCR), B-cell receptor (BCR), CD28, Platelet-derived Growth Factor Receptor (PDGF), nicotinic acetylcholine receptor (nAChR), etc.). The term "linker" as used herein, refers to any agent or molecule that bridges the inventive materials to the targeting moiety. One of ordinary skill in the art recognizes that sites on the inventive materials, which are not necessary for the function of the inventive materials, are ideal sites for attaching a linker and/or a targeting moiety, provided that the linker and/or targeting moiety, once attached to the inventive materials, do(es) not interfere with the function of the inventive materials, i.e., the ability to inhibit proliferation of a diseased cell, or to treat or prevent disease (e.g., cancer, neoplasm, psoriasis).

Alternatively, the inventive materials can be modified into a depot form, such that the manner in which the inventive materials is released into the body to which it is administered is controlled with respect to time and location within the body (see, for example, U.S. Pat. No. 4,450,150). Depot forms of inventive materials can be, for example, an implantable composition comprising the inventive materials and a porous or non-porous material, such as a polymer, wherein the inventive materials is encapsulated by or diffused throughout the material and/or degradation of the non-porous material. The depot is then implanted into the desired location within the body and the inventive materials are released from the implant at a predetermined rate.

It is contemplated that the inventive pharmaceutical compositions, polypeptides (including functional fragments and functional variants), peptidomimetics, fatty acid derivatives, nucleic acids, recombinant expression vectors, host cells, or populations of cells can be used in methods of inhibiting the proliferation of a diseased cell. In this regard, the invention provides a method of inhibiting proliferation of a diseased cell. The method comprises contacting the diseased cell with any of the pharmaceutical compositions described herein in an amount effective to inhibit proliferation of the diseased cell.

In a preferred embodiment of the host, the diseased cell is in a host. The host referred to herein can be any host. Preferably, the host is a mammal. As used herein, the term "mammal" refers to any mammal, including, but not limited to, mammals of the order Rodentia, such as mice and hamsters, and mammals of the order Logomorpha, such as rabbits. It is preferred that the mammals are from the order Carnivora, including Felines (cats) and Canines (dogs). It is more preferred that the mammals are from the order Artiodactyla, including Bovines (cows) and Swines (pigs) or of the order Perssodactyla, including Equines (horses). It is most preferred that the mammals are of the order Primates, Ceboids, or Simoids (monkeys) or of the order Anthropoids (humans and apes). An especially preferred mammal is the human.

The diseased cell can be a cell characteristic of or inflicted with any disease. The disease can be any disease, condition, or malady, especially any of those caused by or involving the proliferation of a cell. The disease can be, for example, a cancer or a non-cancerous tumor, e.g., a cyst, a neoplasm, a fibroma, etc.

The cancer can be any cancer, including any of acute lymphocytic cancer, acute myeloid leukemia, a sarcoma, e.g., alveolar rhabdomyosarcoma, bone cancer, brain cancer, breast cancer, cancer of the anus, anal canal, or anorectum, cancer of the eye, cancer of the intrahepatic bile duct, cancer of the joints, glioma, cancer of the neck, gallbladder, or pleura, cancer of the nose, nasal cavity, or middle ear, cancer of the oral cavity, cancer of the vulva, chronic lymphocytic leukemia, chronic myeloid cancer, colon cancer, esophageal cancer, cervical cancer, gastrointestinal carcinoid tumor, Hodgkin lymphoma, hypopharynx cancer, kidney cancer, larynx cancer, liver cancer, lung cancer, malignant mesothelioma, melanoma, multiple myeloma, nasopharynx cancer, non-Hodgkin lymphoma, ovarian cancer, pancreatic cancer, peritoneum, omentum, and mesentery cancer, pharynx cancer, prostate cancer, rectal cancer, renal cancer (e.g., renal cell carcinoma (RCC)), small intestine cancer, soft tissue cancer, stomach cancer, testicular cancer, thyroid cancer, ureter cancer, and urinary bladder cancer. Preferably, the cancer is breast cancer, prostate cancer, ovarian cancer, stomach cancer (e.g., gastric adenocarcinoma), colon cancer, liver cancer, melanoma, basal cell carcinoma, rhabdomyosarcoma, medulloblastoma, pancreatic cancer, lung cancer, thyroid cancer, a myeloma, a lymphoma, a glioma, or a sarcoma.

As the proliferation of cells can cause a number of diseases, it is further contemplated that the inventive materials described herein can be used in methods of treating or preventing these diseases. In this regard, the invention provides a method of treating or preventing cancer or a neoplasm (e.g., eye neoplasm) in a host. The method comprises administering to the host any of the pharmaceutical compositions described herein in an amount effective to treat the cancer or neoplasm.

The terms "treat," and "prevent" as well as words stemming therefrom, as used herein, do not necessarily imply 100% or complete treatment or prevention. Rather, there are varying degrees of treatment or prevention of which one of ordinary skill in the art recognizes as having a potential benefit or therapeutic effect. In this respect, the inventive methods can provide any amount of any level of treatment or prevention of cancer or a neoplasm in a mammal. Furthermore, the treatment or prevention provided by the inventive method can include treatment or prevention of one or more conditions or symptoms of the disease, e.g., cancer, being treated or prevented. Also, for purposes herein, "prevention" can encompass delaying the onset of the disease, or a symptom or condition thereof.

In a preferred embodiment of the inventive methods, the pharmaceutical composition is topically administered to the host. In another preferred embodiment, the pharmaceutical composition is administered directly to the tumor, e.g., delivered intratumorally.

The invention furthermore provides a method of treating psoriasis in a host comprising administering to the host any of the pharmaceutical compositions described herein in an amount effective to treat psoriasis in the host. Psoriasis is a common skin disease characterized by thickened patches of inflamed, red skin covered with thick, silvery scales. The psoriasis can be any form of psoriasis including, for example, plaque psoriasis, or psoriasis vulgaris, pustular psoriasis, guttate psoriasis, and inverse psoriasis.

The invention also provides a method of inhibiting the Hedgehog signal transduction pathway. The method comprises contacting the diseased cell with any of the pharmaceutical compositions described herein in an amount effective to inhibit the Hedgehog signal transduction pathway. Since expression of certain genes are activated for transcription upon activation of the Hedgehog signal transduction pathway, the invention also provides a method of inhibiting the expression of these genes in a diseased cell. The gene can be one or a combination of: Gli-1 (e.g., GenBank Accession No. NM_005269), Gli-2 (e.g., GenBank Accession No. NM_005270), Gli-3 (e.g., GenBank Accession No. NM_001034190), Ptch (e.g., GenBank Accession No. NM_0000264), Shh (e.g., GenBank Accession No. NM_000193), Smo (e.g., GenBank Accession No. NM_005631), or NES (e.g., GenBank Accession No. NM_016701), which genes are known in the art. The method of inhibiting the expression of these genes comprises contacting the diseased cell with any of the pharmaceutical compositions described herein in an amount effective to inhibit the expression of the gene.

For purposes herein, when a cell, e.g., a diseased cell is contacted with a pharmaceutical composition comprising a nucleic acid or recombinant expression vector, the method involves the expression of the nucleic acid such that the encoded polypeptide (or functional fragment or functional variant) is expressed inside of the cell. When a cell, e.g., a diseased cell is contacted with a pharmaceutical composition comprising a host cell (or a population thereof), the method involves the expression of the nucleic acid inside of the host cell and the secretion of the encoded polypeptide (or functional fragment or functional variant) outside of the host cell where the polypeptide is then available to contact the diseased cell.

The following examples further illustrate the invention but, of course, should not be construed as in any way limiting its scope.

EXAMPLE 1

This example demonstrates a method of preparing polypeptides (including functional fragments and functional variants) in accordance with an embodiment of the invention.

Polypeptides having the amino acid sequences as set forth in Table 1 are synthesized by solid phase peptide synthesis on a 433A Peptide Synthesizer (Applied Biosystems, Foster City, Calif.) equipped with a conductivity monitoring unit utilizing Fmoc amino acid derivatives (AnaSpec, San Jose, Calif.). The synthesis is performed with conditional blocking of unreacted amino groups with acetic anhydride for easier purification of the resulting peptides. Peptides are cleaved from the resin with 87.5% trifluoroacetic acid containing 5% water, 5% thioanisol and 2.5% triisopropyl-silane, precipitated with cold diethyl ether, washed five times with ether and dried in vacuum overnight. Peptides dissolved in dimethylformamide are purified by HPLC on a preparative (25×250 mm) Atlantis C18 reverse phase column (Agilent, Palo Alto, Calif.) in a gradient of 0.05% trifluoroacetic acid in water and acetonitrile containing 0.05% trifluoroacetic acid. The fractions are analyzed by electrospray LC/MS on Agilent 1100 series instrument (Agilent Technologies, Palo Alto, Calif.) with the use of Zorbax 300SB-C18 Poroshell column and a gradient of 5% acetic acid in water and acetonitrile. Only fractions containing more than 95% pure product are combined and freeze-dried. Peptides are dried from 5% acetic acid to ensure conversion into acetate salts. The purity and structure are further confirmed by LC/MS with separation on Zorbax 300SB-C18 analytical column.

TABLE 1

| Peptide Name | Amino acid sequence | SEQ ID NO: |
|---|---|---|
| SMO-i3-1 | PalRGVMTLFSIKSNHPGLLSEKAASKINETMLR | 4 |
| SMO-i3-2 | PalRGVMTLFSIKSNHPGLLSEKA | 9 |
| SMO-i3-4 | PalLFSIKSNHPGLLSEKAASKINETMLR | 10 |
| SMO-i3-5 | RGVMTLFSIKSNHPGLLSEKAASKINETMLRK-ε☐Pal | 60 |
| SMO-i3-6 | LLSEKAASKINETMLRK-☐ ε-Pal | 61 |
| SMO-i3-7 | LFSIKSNHPGLLSEKAASKINETMLRK-☐ ε-Pal | 62 |
| SMO-i3-8 | PalRGVMTLFSIKSNHPGLLS | 14 |
| SMO-i3-9 | PalHseARGVMTLFSIKSNHPGLLS | 77 |
| SMO-i3-10 | PalRGVMTLFSIKSNH | 15 |
| SMO-i3-12 | SEKAASKINETMLRK-☐ ε-Pal | 63 |
| SMOi2-1 | PalLTYAWHTSFKALGTTYQPLSGKYSY | 3 |
| SMOi2-2 | PalLTYAWHTSFKALGTTYQPLSGKTSY | 17 |
| SMOi2-3 | PalLTYAWHTSFKALGTTYQPLSG | 18 |
| SMOi2-4 | AcLTYAWHTSFKALGTTYQPLSGKTSYK-ε-Pal | 64 |
| SMOi2-5 | AcYAWHTSFKALGTTYQPLSGKTSYK-☐ ε-Pal | 65 |
| SMOi2-6 | PalLTYAWHTSFKALGTTYQP | 21 |
| SMOi2-7 | GTTYQPLSGKTSYK-☐ ε-Pal | 66 |
| SMOi2-8 | PalLTYAWHTSFKAL | 23 |
| SMOi2-9 | AcLTYAWHTSFKAL | 24 |
| SM0i2-10 | PalTYAWHTSFKAL | 25 |
| SM0i2-11 | PaILTYAWHTSFKA | 26 |
| SMOi2-12 | PalLTYAWHTSFK | 27 |
| SMOi2-13 | AcTYAWHTSFKA | 28 |
| SMOi2-14 | VWFVVLTYAWHTSFKAL | 55 |
| SM0i2-15 | WFVVLTYAWHTSFKAL | 56 |
| SM0i2-16 | AcLAKFSTHWAYTLK(ε-Pal)-All-D | 67 |
| SMOi2-17 | AcAKFSTHWAYTLK(ε-Pal)-All-D | 68 |
| SMOi2-18 | PalLTYABpaHTSFKAL | 54 |
| SMOi2-20 | AcKFSTHWAYTLK(ε-Pal)All-D | 69 |
| SMOi2-21 | Pal -LTYABpaHTSFKAL-Hcy-Biotin | 81 |
| SMOi2-22 | AKFSTHWAYTL (All-D) | 37 |
| SMOi2-23 | PalLTYAWHTSFKALGTTYQPLSGKTSYK(ε-Pal) | 70 |
| SMOi2-24 | PalLTYAWHTSFKAL (All-D) | 30 |
| SMOi2-25 | AcLTYAWHTSFKAL (All-D) | 31 |
| SMOi2-26 | MyrLTYAWHTSFKAL | 32 |
| SMOi2-29 | Ac-LTYAWHTSFKAL-Penetratin | 82 |
| SM0i2-30 | Penetratin-LTYAWHTSFKAL | 83 |
| SMOi2-56 | AKFSTHWAYTL-β-Ala-α-NH<br>                                 \\<br>                                   K-K-ε-Pal<br>                                 /<br>AKFSTHWAYTL-β-Ala-γ-NH | 84 |
| SMOi2-57 | A D-(LAKFSTHWAYTL)-K-(ε-Pal)-LTYAWHTSFKAL | 92 |
| SM0i2-58 | AD-(AKFSTHWAYTL)-K-(ε-Pal)-LTYAWHTSFKAL | 93 |
| SMOi2-59 | AD-(AKFSTHWAYTL)-K-(ε-Pal)-LTYAWHTSFKA | 94 |

Pal = palmitate;
"all D" = each amino acid of the polypeptide is the D isomer;
Ac = acetate;
Myr = myristate;
PalHse = homoserine palmitate;
Bpa = 4-benzoylphenylalanine; and
HCy-Biotin, homocysteine-Biotin, in which biotin is attached to the SH of homocysteine.

The peptides described herein can be made into a dimeric form having the following general structure:

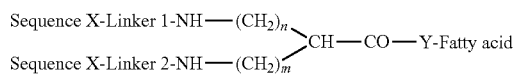

wherein Sequence X is selected from the group consisting of Ac-LAKFSTHWAYTL (all-D) (SEQ ID NO: 85); Ac-AKFSTHWAYTL (All-D) (SEQ ID NO: 86); and Ac—KFSTHWAYTL (All-D) (SEQ ID NO: 87); wherein each of Linker 1 and Linker 2 is optionally present and each independently is Gly, beta-Ala, aminopropionic acid, gamma-aminobutyric acid, aminocaproic acid, or aminohexanoic acid; wherein n and m is between 0 and 6; wherein Y is K, C, homoCys, Orn, diaminopropanoic acid (DPA), diaminobutyric acid (DBA); and wherein the fatty acid is a stearic, palmitic, myristic, lauric, capric or caprilic acid. In a preferred embodiment, Sequence X is SEQ ID NO: 87, n is 4, m is 0, each of Linker 1 and Linker 2 is beta-Ala, and the fatty acid is palmitate.

For the synthesis of such dimeric inhibitors, wherein Y is Lys, resin preloaded with Fmoc-Lys with fatty acid attached to the c-amino group is reacted with a corresponding diamino acid (e.g., Orn, Lys, diaminobutyric acid (DBA), or diaminopropionic acid (DPA)) that has an Fmoc protection group on one amino group and a DDE protection group on the other amino group. The DDE group is selectively removed with a mixture of hydroxylamine and imidazole in DMF. The resulting resin is coupled to a linker amino acid (e.g., Fmoc-Gly, beta-Ala, aminopropionic acid, gamma-aminobutyric acid, aminocaproic acid, or aminohexanoic acid) on an ABI433 peptide synthesizer. The remainder of each Sequence X is simultaneously built on a peptide synthesizer using a standard synthetic protocol. The dimeric product is cleaved, deprotected and purified as in a standard synthetic protocol. SMOi2-56, which is the dimeric form of SMOi2-17, is made in this manner.

SMOi2-29 and -30 are peptides based on SMOi2-9 fused to penetratin, which is a peptide from *Antennapedia* used to introduce a variety of biologically active molecules, such as DNA, peptides, or proteins into cells (Granier et al., *J. Biol. Chem.* 279: 50904-50914 (2004)). Penetratin has the amino acid sequence RQIKIWFPNRR-Nle-KWKK (SEQ ID NO: 78). Penetratin-containing peptides are made as a single peptide chain using standard peptide synthesis methods.

Polypeptides are lipidated as follows: for L-peptides containing ε-palmitoyl-Lys on the C-terminus, commercially available Fmoc-ε-palmitoyl-L-Lys (AnaSpac, San Jose, Calif.) is utilized. Fmoc-ε-palmitoyl-D-Lys is not commercially available. It is synthesized on the resin utilizing orthogonally protected Fmoc-D-Lys(ivDDE) (N-α-Fmoc-N-ε-1-(4,4-dimethyl-2,6-dioxocyclohex-1-ylidene)-3-methyl-butyl-D-lysine) (Novabiochem, San Diego, Calif.). After attachment of the amino acid to Rink-amide resin, ivDDE protection group is removed by treatment with hydrazine/imidazole mixture in NMP. The resin is washed with NMP and reacted with 10-fold excess of palmitic acid/HBTU/HOBt in NMP for two hours. After washing of the resin with NMP, the synthesis is continued utilizing standard protocols on the peptide synthesizer. For peptides comprising myristic acid or acetate at the N-terminus, the corresponding fatty acid (10-fold excess) was dissolved in NMP or NMP/DCM mixture, activated with HBTU/HOBt mixture and reacted with the peptide on the resin. Subsequent cleavage and deprotection was carried out as was done for lipidations with palmitic acid.

The molecular mass of each peptide is determined by ionspray mass spectrometry utilizing an Agilent1100 LC/MS system (Agilent, Santa Clara, Calif.) and is shown in Tables 2 and 3.

TABLE 2

| Compound | Mass (calculated) | Mass (found) | $t_R{}^a$ (min) | Purity |
|---|---|---|---|---|
| SMO i2-1 | 3121.7 | 3121.0 | 16.67 | 95% |
| SMO i2-2 | 3059.6 | 3059.0 | 16.51 | 95% |
| SMO i2-3 | 2580.0 | 2580.0 | 17.13 | 96% |
| SMO i2-4 | 3015.5 | 3015.0 | 16.12 | 95% |
| SMO i2-5 | 3229.8 | 3230.0 | 16.34 | 95% |
| SMO i2-6 | 2225.6 | 2225.5 | 17.13 | 96% |
| SMO i2-7 | 1646.9 | 1647.0 | 18.48 | 98% |
| SMO i2-8 | 1675.1 | 1675.0 | 17.59 | 96% |
| SMO i2-9 | 1478.6 | 1478.0 | 14.64 | 100% |
| SMO i2-10 | 1561.9 | 1562.0 | 18.65 | 98% |
| SMO i2-11 | 1561.9 | 1562.0 | 18.99 | 98% |
| SMO i2-12 | 1490.8 | 1491.0 | 19.04 | 97% |
| SMO i2-13 | 1294.1 | 1294.0 | 13.97 | 99% |
| SMO i2-14 | 2109.4 | 2109.0 | 18.46 | 96% |
| SMO i2-15 | 2010.3 | 2010.0 | 17.86 | 96% |
| SMO i2-16 | 1845.2 | 1845.0 | 18.96 | 97% |
| SMO i2-17 | 1732.1 | 1732.0 | 18.63 | 97% |
| SMOi2-18 | 1740.1 | 1740.0 | 17.75 | 96% |
| SMOi2-20 | 1661.0 | 1661.0 | 17.11 | 98% |
| SMOi2-21 | 2292.3 | 2292.0 | 17.08 | 96% |
| SMOi2-23 | 3426.2 | 3426.0 | 18.00 | 95% |
| SMOi2-24 | 1675.1 | 1674.9 | 17.01 | 96% |
| SMOi2-25 | 1477.9 | 1477.9 | 13.85 | 98% |
| SMOi2-29 | 3689.4 | 3689.0 | 13.95 | 95% |

$^a$The retention times are for Zorbax 300SB-C3 column (Agilent, Santa Clara, CA) determined in 0-100% 25 min gradient of 0.5% acetic acid in water and 0.5% acetic acid in acetonitrile, flow rate of 0.3 mL per minute.

TABLE 3

| Compound | Mass (calculated) | Mass (found) | $t_R{}^a$ (min) | Purity |
|---|---|---|---|---|
| SMOi3-1 | 3630.9 | 3630.9 | 16.08 | 95% |
| SMOi3-2 | 2504.1 | 2504.4 | 16.42 | 96% |
| SMOi3-4 | 3104.8 | 3104.4 | 16.69 | 95% |
| SMOi3-5 | 3801.0 | 3801.0 | 15.87 | 95% |
| SMOi3-6 | 2193.4 | 2193.4 | 15.26 | 96% |
| SMOi3-7 | 3274.9 | 3274.5 | 16.08 | 95% |
| SMOi3-8 | 2176.7 | 2176.2 | 17.05 | 96% |
| SMOi3-10 | 1709.1 | 1708.8 | 17.23 | 97% |
| SMOi3-12 | 1967.4 | 1967.2 | 16.09 | 97% |

$^a$The retention times are for Zorbax 300SB-C3 column (Agilent, Santa Clara, CA) determined in 0-100% 25 min gradient of 0.5% acetic acid in water and 0.5% acetic acid in acetonitrile, flow rate of 0.3 mL per minute.

HPLC of the peptides is performed on a Microsorb-MW 300A C8 column (Varian, Palo Alto, Calif.) in 0-100% 20 min gradient of 0.1% trifluoroacetic acid in water/acetonitrile containing 0.1% trifluoroacetic acid, flow rate 1 ml/min. Peptides are detected by UV monitoring at 225, 256, and 280 nm. Data not shown.

EXAMPLE 2

This example demonstrates a method of testing the inventive polypeptides for toxicity.

DU145 prostate cancer cells, PC3 prostate cancer cells, MCF7 breast cancer cells, or Mel-SK-2 melanoma cells (American Type Culture Collection, Manassas, Va.) are inoculated in 96 well plates at 200-400 cells/well density in DMEM medium containing 10% fetal bovine serum and allowed to attach for 24 hours. Cell suspension of 100 μl is used for each well. Polypeptides in 100 μl medium at 2× concentration are added the next day and kept in the $CO_2$ incubator for 48 hours While the polypeptides are added at a final concentration between 1 nM and 10 μM, assays are performed on extra reference plates to determine the cell population density at time 0 ($T_0$). The cells are stained with Promega Non-Radioactive Cell Proliferation Assay Kit (MTT) according to manufacture's protocol. The absorbance of the wells is determined at 544 nm by a FLUOstar/POLARstar® Galaxy MicroplateReader (BMG Labtechnologies GmbH, Germany). The assays are performed on control (C) and test (T) cells. Cellular responses are calculated from the data using the following formula: $100\times[(T-T_0)/(C-T_0)]$ for $T>T_0$ and $100\times[(T-T_0)/T_0]$ for $T<T_0$.

EXAMPLE 3

This example demonstrates that polypeptides in accordance with embodiments of the invention are able to inhibit proliferation of diseased cells.

Polypeptides corresponding to the full lengths of all three intracellular loops of SMO (SMOi1-1, SMOi2-1, SMOi3-1) having an N-terminal palmitoyl residue are constructed as described in Example 1. The polypeptides are then tested for toxicity (growth inhibition) as described in Example 2 using MCF-7 breast cancer cells and gastric adenocarcinoma cells. Activity of SMOi2-1 and SMOi3-1 is compared to that of cyclopamine (5 μM), a teratogen isolated from the corn lily *Veratrum califonicum*.

Figure 2:
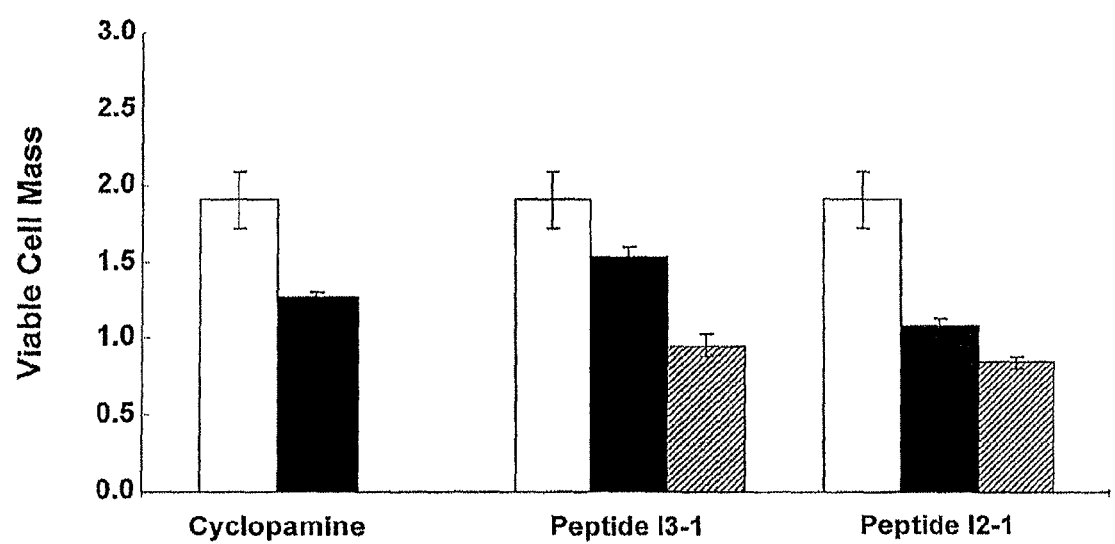
FIG. 2 depicts the viable cell mass of gastric adenocarcinoma cells upon treatment with 0, 5, or 10 µM (white, black, lined bars, respectively) of cyclopamine, SMOi3-1, or SMOi2-1.

As shown in FIG. 1, all three peptides inhibit the growth of MCF-7 cells. The SMOi3-1 polypeptide has the most significant effect on cell growth, followed by SMOi2-1, while SMOi1-1 demonstrates the least amount of inhibitory activity. As shown in FIG. 2, SMOi3-1 and SMOi2-1 polypeptides are able to inhibit the growth of gastric adenocarcinoma cells as well or better than cyclopamine.

EXAMPLE 4

This example demonstrates that functional fragments and functional variants having an amino acid sequence based on the second and third intracellular loops of the SMO protein in accordance with an embodiment of the invention are able to inhibit proliferation of diseased cells.

Polypeptides based on the second or third intracellular loop of SMO (SMOi2 or i3 polypeptides) (as shown in Table 1) are synthesized as described in Example 1 and are tested as described in Example 2 using MCF-7 breast cancer cells or SK-Mel2 melanoma cells. The $IC_{50}$ of each peptide as determined by the MTT assay in SK-Mel2 melanoma cells after 48 hour exposure to the peptide is shown in Tables 4 and 5.

TABLE 4

| Compound | Structure | $IC_{50}$, µM | SEQ ID NO: |
|---|---|---|---|
| SMOi2-1 | Pal-LTYAWHTSFKALGTTYQPLSGKYSY | 0.45 ± 0.05 | 3 |
| SMOi2-2 | Pal-LTYAWHTSFKALGTTYQPLSGKTSY | 0.45 ± 0.05 | 17 |
| SMOi2-3 | Pal-LTYAWHTSFKALGTTYQPLSG | 1.4 ± 0.4 | 18 |
| SMOi2-4 | Ac-LTYAWHTSFKALGTTYQPLSGKTSYK-ϵ-Pal | 1.0 ± 0.1 | 64 |
| SMOi2-5 | Ac-YAWHTSFKALGTTYQPLSGKTSYK-ϵPal | 1.0 ± 0.1 | 65 |
| SMOi2-6 | Pal-LTYAWHTSFKALGTTYQP | 0.3 ± 0.05 | 21 |
| SMOi2-7 | Ac-GTTYQPLSGKTSYK-ϵPal | 2.7 ± 0.4 | 66 |
| SMOi2-8 | Pal-LTYAWHTSFKAL | 0.08 ± 0.02 | 23 |
| SMOi2-9 | Ac-LTYAWHTSFKAL | >10 | 24 |
| SMOi2-10 | Pal-TYAWHTSFKAL | 0.7 ± 0.1 | 25 |
| SMOi2-11 | Pal-LTYAWHTSFKA | 0.09 ± 0.007 | 26 |
| SMOi2-12 | Pal-LTYAWHTSFK | 0.06 ± 0.007 | 27 |
| SMOi2-13 | Ac-TYAWHTSFKA | 2.8 ± 0.3 | 28 |
| SMOi2-14 | VWFVVLTYAWHTSFKAL | >5 | 55 |
| SMOi2-15 | WFVVLTYAWHTSFKAL | >5 | 56 |
| SMOi2-16 | Ac-LAKFSTHWAYTLK-ϵ-Pal (all D-) | 0.006 ± 0.0005 | 67 |
| SMOi2-17 | Ac-AKFSTHWAYTLK-ϵPal (all D-) | 0.0004 ± 0.0001 | 68 |
| SMOi2-18 | Pal-LTYABpaHTSFKAL | 0.1 ± 0.05 | 54 |
| SMOi2-20 | Ac-KFSTHWAYTLK-ϵPal (all D-) | 0.0003 ± 0.0001 | 69 |
| SMOi2-21 | Pal-LTYABpaHTSFKAL-Hcy-Biotin | >15 | 81 |
| SMOi2-23 | Pal-LTYAWHTSFKALGTTYQPLSGKTSYK-ϵ-Pal | 0.05 ± 0.02 | 70 |
| SMOi2-24 | PalLTYAWHTSFKAL (All D) | 0.039 ± 0.004 | 30 |
| SMOi2-25 | AcLTYAWHTSFKAL (All D) | >10 | 31 |
| SMOi2-26 | Myr-LTYAWHTSFKAL | 0.2 ± 0.05 | 32 |
| SMOi2-29 | Ac-LTYAWHTSFKAL-Penetratin | >15 | 82 |
| SMOi2-30 | Penetratin-LTYAWHTSFKAL | >15 | 83 |
| SMOi2-56 | AKFSTHWAYTL-β-Ala-α-NH⟩K-K-ϵ-Pal<br>AKFSTHWAYTL-β-Ala-γ-NH | 4.0 nm | 84 |

Pal, palmitate;
Ac, acetate;
(All D), each amino acid of the polypeptide is the D isomer;
Myr, myristic acid;
ϵ-Pal, palmitate added on the ϵ carbon of Lys;
(Bpa), 4-benzoylphenylalanine.

TABLE 5

| Compound | Structure | $IC_{50}$, µM | SEQ ID NO: |
|---|---|---|---|
| SMO i3-1 | PalRGVMTLFSIKSNHPGLLSEKAASKINETML | 0.64 ± 0.1 | 4 |
| SMO i3-2 | PalRGVMTLFSIKSNHPGLLSEKA | 0.50 ± 0.1 | 9 |
| SMO i3-4 | PalLFSIKSNHPGLLSEKAASKINETMLR | 1.5 ± 0.2 | 10 |
| SMO i3-5 | AcRGVMTLFSIKSNHPGLLSEKAASKINETMLRK-ϵ-Pal | 0.9 ± 0.2 | 60 |
| SMO i3-6 | Ac-LLSEKAASKINETMLRK-☐ϵ-Pal | 0.8 ± 0.1 | 61 |
| SMO i3-7 | Ac-LFSIKSNHPGLLSEKAASKINETMLRK-☐ϵ-Pal | 0.95 ± 0.2 | 62 |
| SMO i3-8 | PalRGVMTLFSIKSNHPGLLS | 0.5 ± 0.1 | 14 |
| SMO i3-10 | PalRGVMTLFSIKSNH | 0.95 ± 0.2 | 15 |
| SMO i3-12 | SEKAASKINETMLRK-ϵ-Pal | 1.33 ± 0.2 | 63 |

Figure 3:
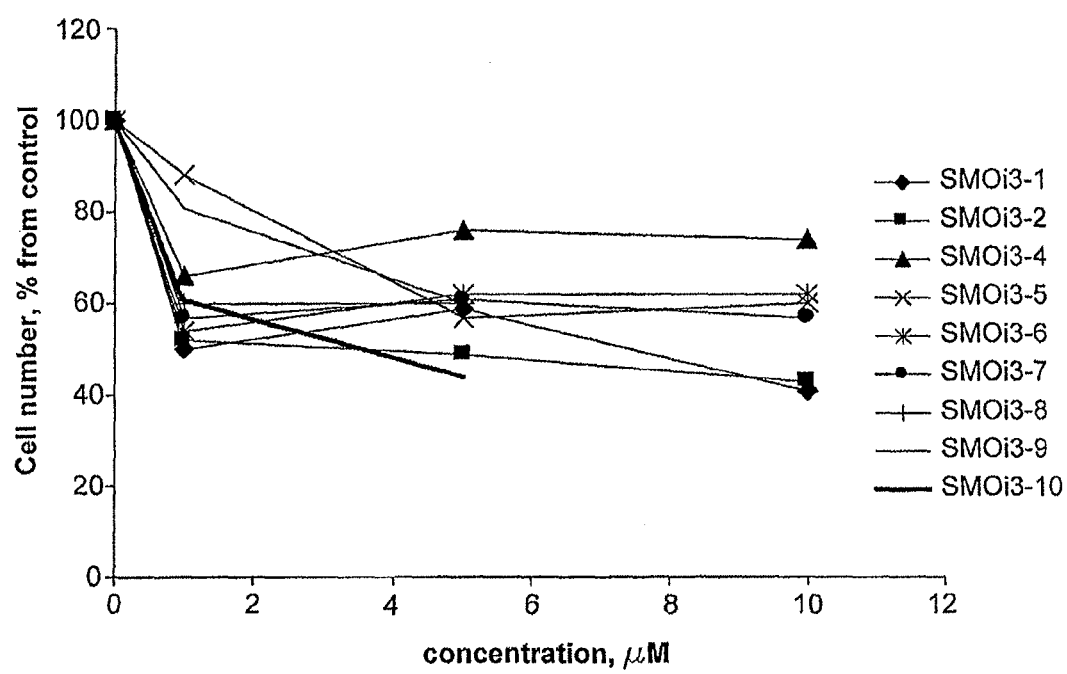
FIG. 3 depicts the % of viable MCF-7 cells (relative to a control) upon a 48-hour treatment with polypeptides comprising amino acid sequences based on the third intracellular loop of the SMO protein, in accordance with an embodiment of the invention.

As shown in Table 5 and FIG. 3, polypeptides based on the third intracellular loop of SMO exhibit the ability to inhibit the growth of MCF-7 cells. Also, peptides corresponding to fragments of the third intracellular loop have activities that are comparable or lower than the full-length loop (SMOi3-1).

As shown in Table 4, several of the polypeptides based on the second intracellular loop of SMO (SMOi2 polypeptides) are able to inhibit the growth of SK-Mel2 melanoma cells after 48 hours of exposure to the polypeptides. Among the most potent inhibitors are SMOi2-16, SMOi2-17, SMOi2-8, SMOi2-23, SMOi2-24, SMOi2-20, SMOi2-26, SMOi2-11, and SMOi2-12. Also, SMOi2-6, SMOi2-7, SMOi2-2 through SMOi2-5, SMOi2-10, and SMOi2-13 are potent inhibitors. C-terminal truncation of the second intracellular loop yields polypeptides that were significantly more toxic to cancer cells than the full-length loop (SMOi2-1). Both halves of the loop when palmitoylated at the amino acids which are positioned at the end of the loop (which end is adjacent to the membrane in the wild-type SMO protein) are active. However, C-terminal extension of the N-terminal half lowers the activity of the most potent 12-residue long polypeptide (compare peptides SMOi2-8 with SMOi2-6 and SMOi2-3).

Palmitic acid lipidation of the polypeptides appears to be essential for the activity, since substitution of palmitate with an acetyl residue significantly reduces the inhibitory activity (compare SMOi2-9 and SMOi2-13). This is likely due to poor cell penetration of the polypeptide. It appears necessary for the palmitoylation to occur at the end of the loop (which end is adjacent to the membrane in the wild-type SMO protein), since positioning the palmitoyl group inside the loop generated a significantly less active peptide (SMOi3-4 of Table 5). The growth inhibition curves of these polypeptides either plateau at higher concentrations or curve upward, indicating that inhibitory activity actually decreases at higher concentrations. SMOi3-1, SMOi3-8, SMOi3-2, SMOi3-6, and SMOi3-12 are among the most potent polypeptides tested.

Unlike SMOi3 polypeptides, all second loop derivatives have "normal" concentration-dependence profiles of growth inhibition activity.

As an alternative delivery of the peptides inside the cells, SMOi2-9 is fused to penetratin. Neither C-terminal nor N-terminal fusion helps to restore the activity, suggesting that palmitoylation provides more than just cell permeability. Also, the replacement of palmitoyl residue with sequences of the transmembrane domain of the SMO protein does not overcome the loss of activity (SMOi2-14 and SMOi2-15). The lack of activity may be due to the fact that these polypeptides have poor solubility. Substitution of palmitoyl residue with slightly shorter myristoyl resulted in 2.5-fold less potent compound (SMOi2-26). For studying peptide localization inside the cells and characterization of the interacting protein molecules, synthesis of cross-linkable derivative labeled with biotin is attempted. Substitution of Trp residue of SMOi2-8 with p-benzoyl-phenylalanine that can be UV cross-linked to a protein ligand produces a fairly active compound (SMOi2-18, Table 4). However, addition of maleimide-biotin coupled through SH-group of C-terminal homocysteine (SMOi2-21) totally abolishes the activity, thus rendering it unsuitable for receptor identification.

Figure 4:
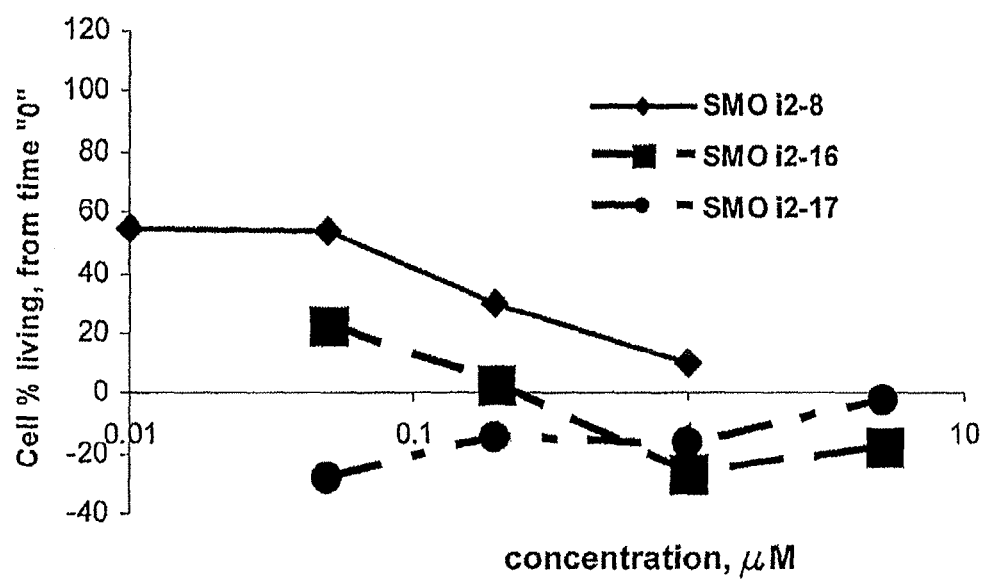
FIG. 4 depicts the % of viable SK-Mel2 cells upon a 48-hour treatment with SMOi2-8 or retroinverso analogues, SMOi2-16 and SMOi2-17, in accordance with an embodiment of the invention.
Figure 7:
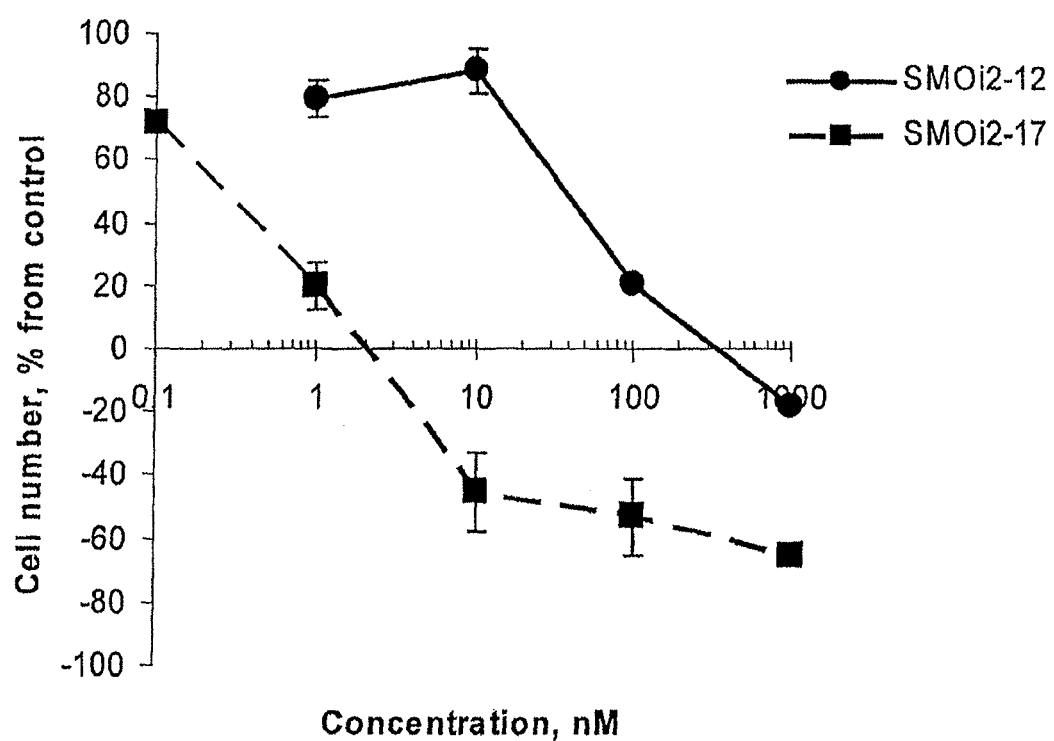
FIG. 7 depicts the toxicity of the second intracellular loop derivatives (SMOi2-12 (circles) and SMOi2-17 (squares)) as determined by MTT assay in SK-Mel2 melanoma cells after 48 h of exposure to the peptide compounds, in accordance with an embodiment of the invention.

The retroinverso analogues of SMOi2 polypeptides exhibit inhibitory activity. Both SMOi2-16, which is the retroinverso analogue of SMOi2-8, and its truncated version SMOi2-17, which is the retroinverso analogue of SMOi2-11 (and SMOi2-12), are more potent in inhibiting and killing melanoma cells than their all-L parent polypeptide (FIGS. 4 and 7).

EXAMPLE 5

This example demonstrates a method of inhibiting the gene expression of Hedgehog signaling pathway proteins in cells in accordance with an embodiment of the invention.

An analysis of expression of the genes that are known markers of the Hedgehog signal transduction pathway, Gli-1, Gli-2, Gli3, Ptch, Shh, Smo and NES is performed. DU145 prostate cancer cells are exposed to SMOi3-1 (5 or 10 µM), SMOi2-1 (5 or 10 µM) or cyclopamine (5 µM) for 48 hours. Gene expression is assayed by quantitative PCR. For gene expression assay, DU145 prostate cancer cells were exposed to 5 µM SMOi3-1 for 24 h, and 5 µM and 10 µM SMOi3-1 for 48 h, respectively. DU145 cells were treated by 5 µM and 10 µM of SMOi2-1 for 24 h only. The control was DU145 cells without compounds-treatment. The 5 µM of cyclopamine was always used as positive control in all experiments.

Total cellular RNA was isolated, and further purified by RNeasy® columns (QIAGEN, Valencia, Calif.) according to the manufacturer's instructions. RNA quality and quantity were determined using Agilent RNA 6000 Nano Chip (Agilent Technologies, Inc., CA). cDNA synthesis was carried out using Random Hexamer primer, TaqMan® Reverse Transcription Reagents kit (Applied Biosystems, Foster, Calif.).

Taqman® Gene Expression Assay primer and probe (FAM-labeled) sets (Applied Biosystems, Foster, Calif.) are used for real-time quantitative PCR analysis of PTCH (Assay ID=Hs00181117_m1), GUI (Hs00171790_m1), GLI2 (Hs00257977_ml), GLI3 (Hs00609233_m1), SMO (Hs00170665_m1), SHH (Hs00179843_m1) and NES (Hs00707120_s1). TaqMan® Gene Expression Assay mix of primer and probe (VIC-labeled) of 18S rRNA was used as the endogenous control. Each sample is run in triplicate. Triplicate Ct values were analyzed using the comparative Ct ($\Delta\Delta Ct$) method as described by the manufacturer (Applied Biosystems, Foster, Calif.). The relative amount of target ($2^{-\Delta\Delta Ct}$) is obtained by normalization to an endogenous reference (18s rRNA).

Figure 5:
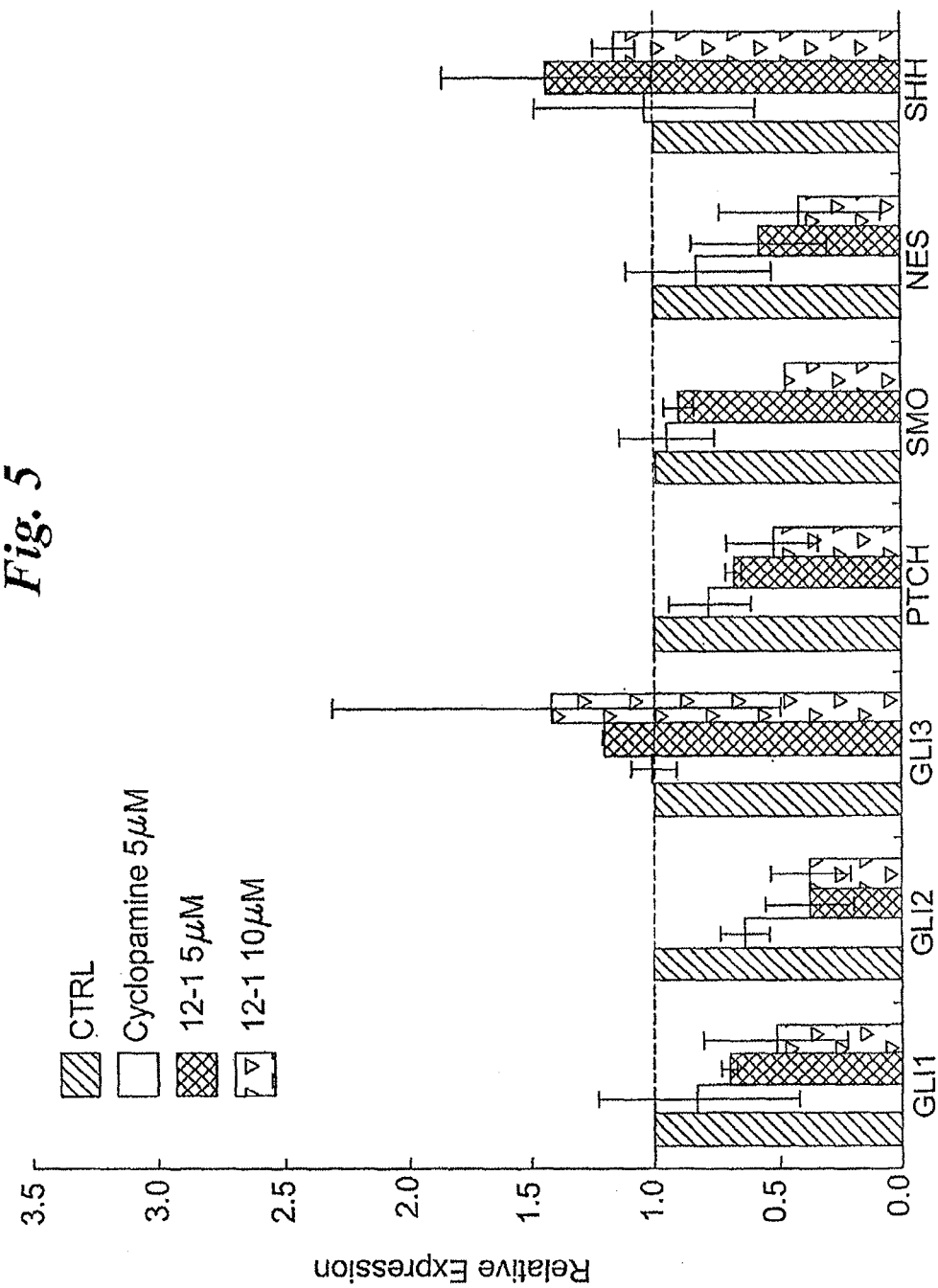
FIG. 5 depicts the relative expression of genes of the HH pathway in DU145 cells upon a 48-hour treatment with cyclopamine, SMOi3-1, or SMOi2-1 polypeptides, in accordance with an embodiment of the invention.

As shown in FIG. 5, the changes in gene expression are more pronounced than that of SMO antagonist, cyclopamine. This is consistent with the fact that the polypeptides have a much higher potency than cyclopamine.

EXAMPLE 6

This example demonstrates that inventive peptidomimetics in accordance with embodiments of the invention inhibit the proliferation of diseased cells.

Peptides SMOi2-18 and SMOi2-21 are made as essentially described in Example 1 and tested as described in Example 2 using SK-Mel2 cells. Cells are exposed to polypeptides or peptidomimetics for 60 hours.

Figure 6:
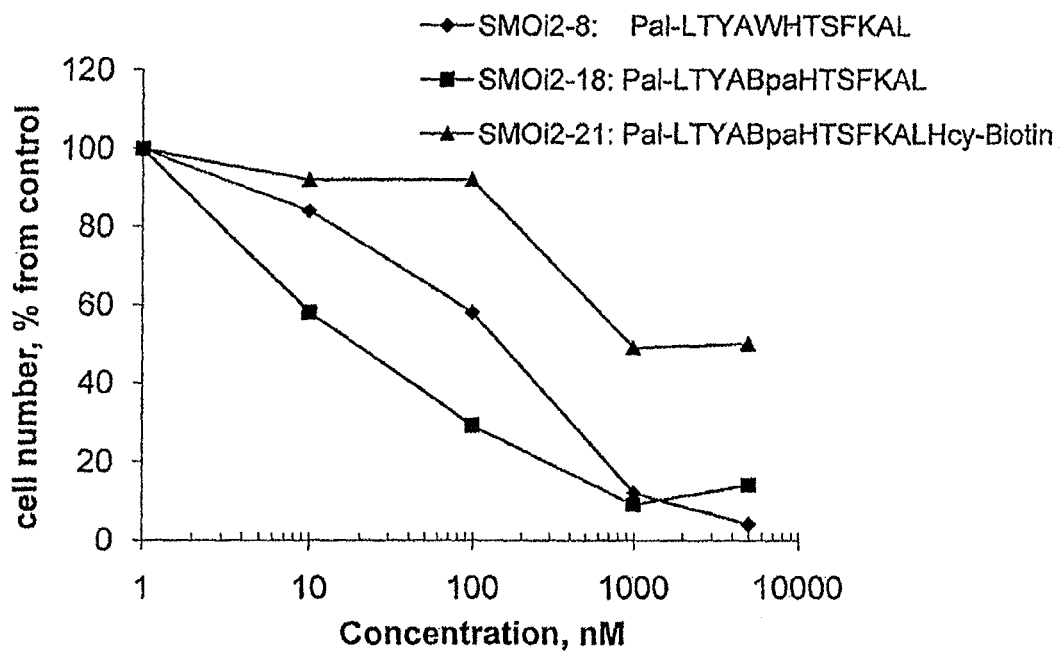
FIG. 6 depicts the % of viable SK-Me12 cells upon a 60-hour treatment with SMOi2-8 (SEQ ID NO: 23) or peptidomimetics containing a 4-benzoylphenylalanine (BPA) residue in place of the Trp residue at position 5 of SMOi2-8, SMOi2-18 (SEQ ID NO: 54) or SMOi2-21 (SEQ ID NO: 81), in accordance with an embodiment of the invention.

As shown in FIG. 6, peptidomimetics, SMOi2-18 and SMOi2-21, each of which contains the synthetic amino acid, BPA, exhibit the ability to inhibit the proliferation of SK-Mel2 cells. The inhibitory activity is even more potent than that of the polypeptide counterpart, SMOi2-8, which contains only naturally-occurring amino acids.

EXAMPLE 7

This example demonstrates the critical micelle concentration of SMOi2-8.

To monitor the formation of hydrophobic nanoparticles, a fluorescing imidazoacridone compound WMC-77 (5-{3-[4-(aminopropyl)-piperazin-1-yl]-propylamino}-2,10b-diazaaceanthrylen-6-one) is used (Tarasov et al., *Photochem. Pho-* tobiol. 78: 313-322 (2003)). Compounds like WMC-77 tend to enhance their intrinsic fluorescence dramatically when entering an amphiphilic environment of biological macromolecules like DNA (Tarasova et al., 2003, supra) or hydrophobic core of typical micelles (Tarasov et al., *Photochem. Photobiol.* 70: 568-578 (1999)). Since imidazoacridones are adsorbed on quartz from the aqueous solutions, plastic polymethacrylate 10×10 mm cells from Sigma-Aldrich (St. Louis, Mo.) are used for most measurements. Atmospheric oxygen quenching is found to be unimportant, since similar values of fluorescence intensity from BIAs are obtained before and after nitrogen purging. The solutions are prepared in deionized water. Uncorrected fluorescence emission spectra are obtained at 25° C. on a Single Photon Counting Spectrofluorometer FLUOROMAX®-2 (Horiba Jobin Yvon, Edison, N.J.). The excitation and emission monochromator slits are adjusted to 1.5 and 3.5 nm bandwidth, respectively. The emission spectra (increment 1 nm, integration time 0.2 sec.) are collected at the range 450-700 nm, using 430 nm excitation monochromator setting. The fluorometric measurements are performed for premixed aliquots of peptide and imidazoacridone solutions. The concentration of fluorescing agent WMC-77 in all probes is 0.4 μM.

Figure 8:
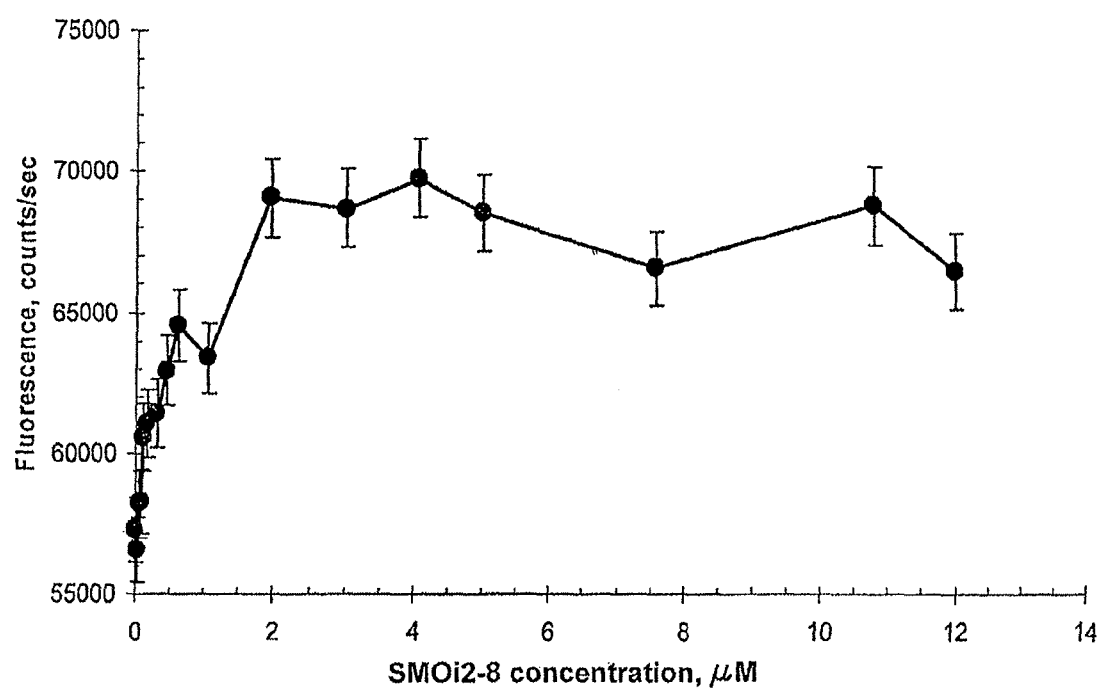
FIG. 8 depicts the fluorescence emission intensity measured for probes with increasing SMOi2-8/WMC-77 ratio, in accordance with an embodiment of the invention.

The fluorescence data are presented in FIG. 8. The increase of peptide/fluorophore ratio causes the permanent increase of WMC-77 fluorescence emission intensity, leveling of at ~2 μM. The changes in the fluorescence signal are similar to those observed during transfer of imidazoacridones from aqueous to non-polar media such as organic solvents (Tarasov et al., 1999, supra), to the cores of classic surfactant micelles (Tarasov et al., 1999, supra) or upon binding to DNA (Tarasov et al., 2003, supra). The critical micelle concentration, estimated as described in (Tanford, *The Hydrophobic Effect: Formation of Micelles and Biological Membranes*, John Wiley & Sons, New York (1980)), is determined as 0.5-1 μM of SMOi2-8.

Critical micelle concentration is tested as described above for all other peptides of this study and is found to be around 1 μM for each peptide. Micellization may be responsible for lowering the effective concentration of free peptides in solution and subsequent apparent reduction in potency. The majority of peptides also precipitated out in medium at concentration higher than 10 μM.

EXAMPLE 8

This example demonstrates that the peptides of the invention exhibit different sensitivities toward different cell lines.

Figure 9:
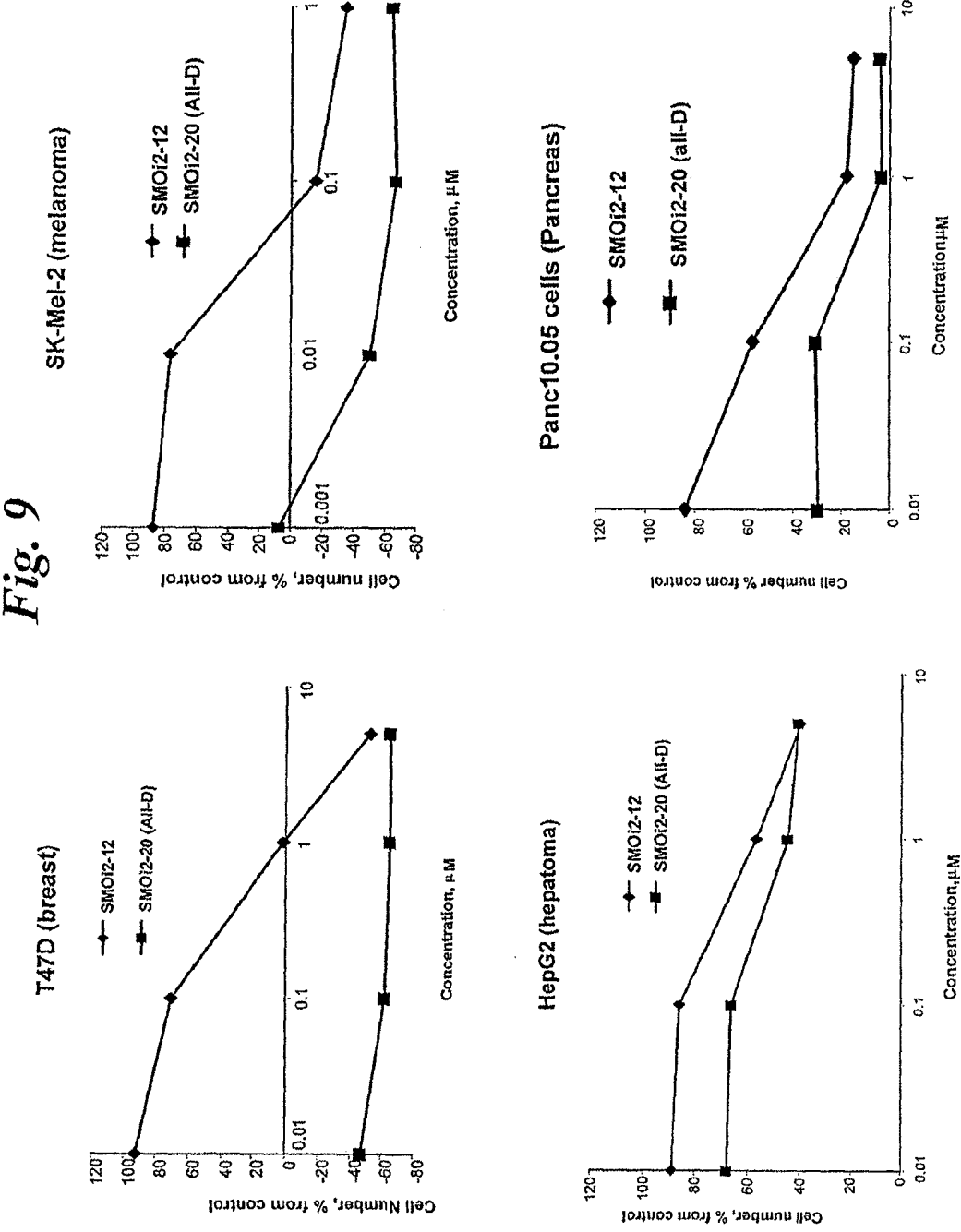
FIG. 9 depicts the growth inhibition of breast cancer, melanoma, heptaoma, and pancreatic cancer cells upon exposure to SMOi2-12 (diamonds) or SMOi2-20 (squares), in accordance with an embodiment of the invention.

Cancer cells of the breast (T47D), melanoma (SK-MEL-2), hepatoma (HepG2, PLC, JM-1), pancreas (Panc10.05, HS766T), colon (Colo205, HCT15), and lung (A549) are cultured in medium containing either SMOi2-12 or SMOi2-20 at a concentration of 0.001, 0.01, 0.1, 1.0, or 5 μM. Cells are assayed as described in Example 2. As shown in FIG. 9, SMOi2-12 and SMOi2-20 exhibit different sensitivities depending on the cell treated. Cell lines exhibiting a $GI_{50}$>5 include PLC, JM-1, HS766T, Colo205, HCT15, and A549.

EXAMPLE 9

This example demonstrates the peptides of the invention have secondary structure.

The peptides are measured by circular dichroism (CD) spectroscopy. Peptide solutions (1 μM) are prepared by dissolving compounds in PBS containing 50 mM dodecylphophocholine (Avanti Polar Lipids, Alabaster, Ala.). CD spectra are recorded by an AVIV mod. 202 CD-spectrometer (Aviv Instruments, Lakewood, N.J.) using 0.1 cm path length quartz cuvette at 22-24° C. Scan ranges are between 180 and 260 nm and the spectrum of the buffer is subtracted from the spectrum of the compound.

Figure 10:
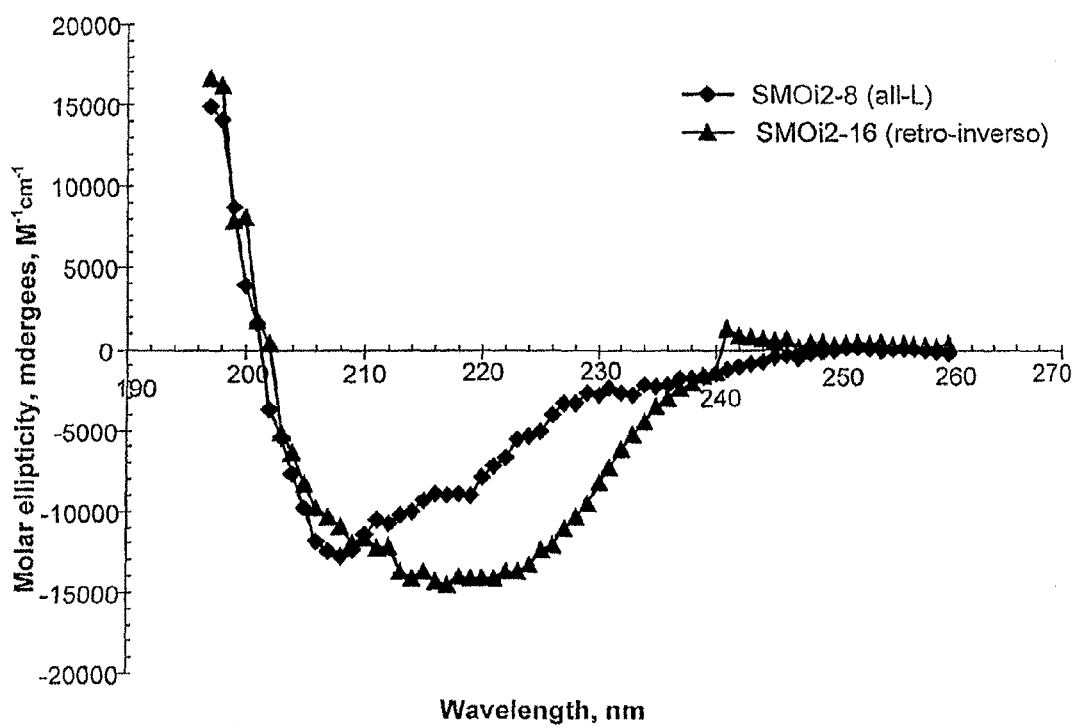
FIG. 10 depicts the circular dichroism spectrum of SMOi2-8 (diamonds) and SMOi2-16 (triangles) peptides.

The CD spectra of SMOi2-8 and SMOi2-16 (FIG. 10) demonstrate that the peptides predominantly adopt a beta-strand conformation. The retro-inverso peptides appear to be more structured and rigid than the parent all-L counterparts.

EXAMPLE 10

The example demonstrates alanine scanning studies of the polypeptides of the invention.

The significance of different residues in the SMOi2-8 sequence (PalLTYAWHTSFKAL) (SEQ ID NO: 23) is probed by creating a collection of mutants of the SMOi2-8 peptides in which each mutant of the collection has an amino acid residue substituted with Ala and every residue of SMOi2-8 is targeted for mutation by at least one of the mutants in the collection.

The Lys residue at the 10th position of SMOi2-8 is critical for the activity of the SMOi2-8 peptide. Significant loss in activity also is observed upon substitution of the Ser at position 8 of SMOi2-8. Activity increased when the Leu at position 1 was replaced with Ala. The Phe at position 9, Tyr at position 3, and Trp at position 5 can be substituted with Ala without significant change in the activity. The remaining substitutions (2, 4, 6, 7, 11, and 12) result in a slight (40-60%) increase in $GI_{50}$.

All references, including publications, patent applications, and patents, cited herein are hereby incorporated by reference to the same extent as if each reference were individually and specifically indicated to be incorporated by reference and were set forth in its entirety herein.

The use of the terms "a" and "an" and "the" and similar referents in the context of describing the invention (especially in the context of the following claims) are to be construed to cover both the singular and the plural, unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Preferred embodiments of this invention are described herein, including the best mode known to the inventors for carrying out the invention. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

The invention claimed is:

1. An isolated or purified polypeptide or a fatty acid derivative of the polypeptide, wherein the polypeptide consists of the amino acid sequence of SEQ ID NO: 4 or a functional fragment of SEQ ID NO: 4, wherein the functional fragment consists of the amino acid sequence of any one of SEQ ID NOs: 6 and 9-16 and the amino acid at position 1 of the polypeptide is optionally acetylated.

2. The isolated or purified polypeptide or fatty acid derivative of claim 1, wherein the polypeptide consists of the amino acid sequence of SEQ ID NO: 4.

3. The isolated or purified polypeptide or fatty acid derivative of claim 1, wherein the polypeptide consists of the amino acid sequence of SEQ ID NO: 6.

4. The isolated or purified polypeptide or fatty acid derivative of claim 1, wherein the polypeptide consists of the amino acid sequence of SEQ ID NO: 9.

5. The isolated or purified polypeptide or fatty acid derivative of claim 1, wherein the polypeptide consists of the amino acid sequence of SEQ ID NO: 10.

6. The isolated or purified polypeptide or fatty acid derivative of claim 1, wherein the polypeptide consists of the amino acid sequence of SEQ ID NO: 11.

7. The isolated or purified polypeptide or fatty acid derivative of claim 1, wherein the polypeptide consists of the amino acid sequence of SEQ ID NO: 12.

8. The isolated or purified polypeptide or fatty acid derivative of claim 1, wherein the polypeptide consists of the amino acid sequence of SEQ ID NO: 13.

9. The isolated or purified polypeptide or fatty acid derivative of claim 1, wherein the polypeptide consists of the amino acid sequence of SEQ ID NO: 14.

10. The fatty acid derivative of claim 1, wherein the fatty acid derivative comprises a fatty acid molecule at the amino (N—) terminus, the carboxyl (C—) terminus, or both the N- and C-termini of the polypeptide, the fatty acid derivative optionally containing at least one amino acid linker.

11. The fatty acid derivative of claim 10, wherein, when the fatty acid molecule is at the C-terminus, the fatty acid molecule is attached to the polypeptide through an amino acid linker selected from the group consisting of Lys, Cys, homocysteine, ornithine, α,γ-diaminobutyric acid, and α,β-diaminopropionic acid.

12. The fatty acid derivative of claim 11, wherein the amino acid linker is Lys.

13. The fatty acid derivative of claim 10, wherein the fatty acid molecule is a $C_8$ to $C_{20}$ fatty acid.

14. The fatty acid derivative of claim 13, wherein the fatty acid molecule is a $C_{16}$ fatty acid.

15. The fatty acid derivative of claim 10, wherein, when the fatty acid molecule is at the C-terminus, the fatty acid molecule is a molecule of Formula I or Formula II, wherein Formula I is $NH_2(CH_2)_nCOOH$ and Formula II is $CH_3(CH_2)_mCH(NH_2)COOH$, wherein each of n and m is 8-16.

16. The fatty acid derivative of claim 15, wherein n or m is 16.

17. The isolated or purified polypeptide or fatty acid derivative of claim 1, which is linked to a cell-penetrating peptide (CPP).

18. The isolated or purified polypeptide or fatty acid derivative of claim 17, wherein the CPP comprises the amino acid sequence of SEQ ID NO: 78 or 79.

19. The fatty acid derivative of claim 10 consisting of the amino acid sequence of any one of SEQ ID NOs: 60-63, wherein the amino acid at position 1 of the polypeptide is optionally acetylated.

20. The fatty acid derivative of claim 10 consisting of the amino acid sequence of SEQ ID NO: 60, wherein the amino acid at position 1 of the polypeptide is optionally acetylated.

21. A conjugate comprising (i) the polypeptide or fatty acid derivative of claim 1 and (ii) a targeting moiety.

22. The fatty acid derivative of claim 10 consisting of the amino acid sequence of SEQ ID NO: 61, wherein the amino acid at position 1 of the polypeptide is optionally acetylated.

23. The fatty acid derivative of claim 10 consisting of the amino acid sequence of SEQ ID NO: 62, wherein the amino acid at position 1 of the polypeptide is optionally acetylated.

24. The fatty acid derivative of claim 10 consisting of the amino acid sequence of SEQ ID NO: 63, wherein the amino acid at position 1 of the polypeptide is optionally acetylated.

25. A pharmaceutical composition comprising the fatty acid derivative of claim 1 and a pharmaceutically acceptable carrier.

26. A pharmaceutical composition comprising the conjugate comprising the fatty acid derivative of claim 21 and a pharmaceutically acceptable carrier.

27. The isolated or purified polypeptide or fatty acid derivative of claim 1, wherein the polypeptide consists of the amino acid sequence of SEQ ID NO: 15.

28. The isolated or purified polypeptide or fatty acid derivative of claim 1, wherein the polypeptide consists of the amino acid sequence of SEQ ID NO: 16.

29. The pharmaceutical composition of claim 25, wherein the pharmaceutical composition is a topical formulation.

30. The pharmaceutical composition of claim 29, wherein the topical formulation is a cream, a lotion, an ointment, or a patch.

31. The pharmaceutical composition of claim 30, wherein the lotion also includes an ultraviolet (UV) light blocking agent.

32. The pharmaceutical composition of claim 25, wherein the pharmaceutical composition is an intravenous formulation or a subcutaneous formulation.

33. A method of inhibiting proliferation of a tumor cell, comprising locally contacting the tumor cell with the pharmaceutical composition of claim 25 in an amount effective to inhibit proliferation of the tumor cell.

34. The method of claim 33, wherein the tumor cell is in a host.

35. The method of claim 34, wherein the host is a mammal.

36. The method of claim 35, wherein the mammal is a human.

37. The method of claim 33, wherein the method treats a cancer of a host.

38. The method of claim 37, wherein the cancer is breast cancer, prostate cancer, ovarian cancer, stomach cancer, colon cancer, liver cancer, melanoma, basal cell carcinoma, rhabdomyosarcoma, a medulloblastoma, pancreatic cancer, lung cancer, thyroid cancer, a myeloma, a lymphoma, a glioma, or a sarcoma.

39. The method of claim 38, wherein the stomach cancer is a gastric adenocarcinoma.

40. The method of claim 33, wherein the method treats a neoplasm of a host.

41. The method of claim 33, wherein the pharmaceutical composition is topically administered to the host.

42. The method of claim 33, wherein the pharmaceutical composition is intratumorally administered to the host.

43. A method of treating cancer in a host comprising locally administering to the host a pharmaceutical composition of claim 25 in an amount effective to treat the cancer.

44. A method of treating a neoplasm in a host comprising locally administering to the host a pharmaceutical composition of claim 25 in an amount effective to treat the neoplasm.

45. A method of inhibiting the expression of a gene selected from the group consisting of Gli-1, Gli-2, Gli-3, Ptch, Shh, Smo, NES, and a combination thereof, in a tumor cell, comprising contacting the tumor cell with a pharmaceutical composition of claim 25 in an amount effective to inhibit the expression of the gene.

46. A method of inhibiting the Hedgehog signal transduction pathway in a tumor cell, comprising contacting the tumor cell with a pharmaceutical composition of claim 25 in an amount effective to inhibit the Hedgehog signal transduction pathway.

* * * * *

SEQUENCE LISTING

<160> NUMBER OF SEQ ID NOS: 94

<210> SEQ ID NO 1
<211> LENGTH: 787
<212> TYPE: PRT
<213> ORGANISM: Homo sapiens
<220> FEATURE:
<221> NAME/KEY: MISC_FEATURE
<223> OTHER INFORMATION: Genbank NP_005622

<400> SEQUENCE: 1

Met Ala Ala Ala Arg Pro Ala Arg Gly Pro Glu Leu Pro Leu Leu Gly
1               5                   10                  15

Leu Leu Leu Leu Leu Leu Leu Gly Asp Pro Gly Arg Gly Ala Ala Ser
            20                  25                  30

Ser Gly Asn Ala Thr Gly Pro Gly Pro Arg Ser Ala Gly Gly Ser Ala
        35                  40                  45

Arg Arg Ser Ala Ala Val Thr Gly Pro Pro Pro Leu Ser His Cys
    50                  55                  60

Gly Arg Ala Ala Pro Cys Glu Pro Leu Arg Tyr Asn Val Cys Leu Gly
65                  70                  75                  80

Ser Val Leu Pro Tyr Gly Ala Thr Ser Thr Leu Leu Ala Gly Asp Ser
                85                  90                  95

Asp Ser Gln Glu Glu Ala His Gly Lys Leu Val Leu Trp Ser Gly Leu
            100                 105                 110

Arg Asn Ala Pro Arg Cys Trp Ala Val Ile Gln Pro Leu Leu Cys Ala
        115                 120                 125

Val Tyr Met Pro Lys Cys Glu Asn Asp Arg Val Glu Leu Pro Ser Arg
    130                 135                 140

Thr Leu Cys Gln Ala Thr Arg Gly Pro Cys Ala Ile Val Glu Arg Glu
145                 150                 155                 160

Arg Gly Trp Pro Asp Phe Leu Arg Cys Thr Pro Asp Arg Phe Pro Glu
                165                 170                 175

Gly Cys Thr Asn Glu Val Gln Asn Ile Lys Phe Asn Ser Ser Gly Gln
            180                 185                 190

Cys Glu Val Pro Leu Val Arg Thr Asp Asn Pro Lys Ser Trp Tyr Glu
        195                 200                 205

Asp Val Glu Gly Cys Gly Ile Gln Cys Gln Asn Pro Leu Phe Thr Glu
    210                 215                 220

Ala Glu His Gln Asp Met His Ser Tyr Ile Ala Phe Gly Ala Val
225                 230                 235                 240

Thr Gly Leu Cys Thr Leu Phe Thr Leu Ala Thr Phe Val Ala Asp Trp
                245                 250                 255

Arg Asn Ser Asn Arg Tyr Pro Ala Val Ile Leu Phe Tyr Val Asn Ala
            260                 265                 270

Cys Phe Phe Val Gly Ser Ile Gly Trp Leu Ala Gln Phe Met Asp Gly
        275                 280                 285

Ala Arg Arg Glu Ile Val Cys Arg Ala Asp Gly Thr Met Arg Leu Gly
    290                 295                 300

Glu Pro Thr Ser Asn Glu Thr Leu Ser Cys Val Ile Ile Phe Val Ile
305                 310                 315                 320

Val Tyr Tyr Ala Leu Met Ala Gly Val Val Trp Phe Val Val Leu Thr
                325                 330                 335

Tyr Ala Trp His Thr Ser Phe Lys Ala Leu Gly Thr Thr Tyr Gln Pro
            340                 345                 350

-continued

```
Leu Ser Gly Lys Thr Ser Tyr Phe His Leu Thr Trp Ser Leu Pro
        355                 360                 365

Phe Val Leu Thr Val Ala Ile Leu Ala Val Ala Gln Val Asp Gly Asp
370                 375                 380

Ser Val Ser Gly Ile Cys Phe Val Gly Tyr Lys Asn Tyr Arg Tyr Arg
385                 390                 395                 400

Ala Gly Phe Val Leu Ala Pro Ile Gly Leu Val Leu Ile Val Gly Gly
                405                 410                 415

Tyr Phe Leu Ile Arg Gly Val Met Thr Leu Phe Ser Ile Lys Ser Asn
                420                 425                 430

His Pro Gly Leu Leu Ser Glu Lys Ala Ala Ser Lys Ile Asn Glu Thr
            435                 440                 445

Met Leu Arg Leu Gly Ile Phe Gly Phe Leu Ala Phe Gly Phe Val Leu
450                 455                 460

Ile Thr Phe Ser Cys His Phe Tyr Asp Phe Phe Asn Gln Ala Glu Trp
465                 470                 475                 480

Glu Arg Ser Phe Arg Asp Tyr Val Leu Cys Gln Ala Asn Val Thr Ile
                485                 490                 495

Gly Leu Pro Thr Lys Gln Pro Ile Pro Asp Cys Glu Ile Lys Asn Arg
                500                 505                 510

Pro Ser Leu Leu Val Glu Lys Ile Asn Leu Phe Ala Met Phe Gly Thr
            515                 520                 525

Gly Ile Ala Met Ser Thr Trp Val Trp Thr Lys Ala Thr Leu Leu Ile
530                 535                 540

Trp Arg Arg Thr Trp Cys Arg Leu Thr Gly Gln Ser Asp Asp Glu Pro
545                 550                 555                 560

Lys Arg Ile Lys Lys Ser Lys Met Ile Ala Lys Ala Phe Ser Lys Arg
                565                 570                 575

His Glu Leu Leu Gln Asn Pro Gly Gln Glu Leu Ser Phe Ser Met His
            580                 585                 590

Thr Val Ser His Asp Gly Pro Val Ala Gly Leu Ala Phe Asp Leu Asn
            595                 600                 605

Glu Pro Ser Ala Asp Val Ser Ser Ala Trp Ala Gln His Val Thr Lys
610                 615                 620

Met Val Ala Arg Arg Gly Ala Ile Leu Pro Gln Asp Ile Ser Val Thr
625                 630                 635                 640

Pro Val Ala Thr Pro Val Pro Pro Glu Glu Gln Ala Asn Leu Trp Leu
                645                 650                 655

Val Glu Ala Glu Ile Ser Pro Glu Leu Gln Lys Arg Leu Gly Arg Lys
                660                 665                 670

Lys Lys Arg Arg Lys Arg Lys Lys Glu Val Cys Pro Leu Ala Pro Pro
            675                 680                 685

Pro Glu Leu His Pro Pro Ala Pro Ala Pro Ser Thr Ile Pro Arg Leu
            690                 695                 700

Pro Gln Leu Pro Arg Gln Lys Cys Leu Val Ala Ala Gly Ala Trp Gly
705                 710                 715                 720

Ala Gly Asp Ser Cys Arg Gln Gly Ala Trp Thr Leu Val Ser Asn Pro
                725                 730                 735

Phe Cys Pro Glu Pro Ser Pro Pro Gln Asp Pro Phe Leu Pro Ser Ala
                740                 745                 750

Pro Ala Pro Val Ala Trp Ala His Gly Arg Arg Gln Gly Leu Gly Pro
            755                 760                 765
```

```
Ile His Ser Arg Thr Asn Leu Met Asp Thr Glu Leu Met Asp Ala Asp
        770                 775                 780

Ser Asp Phe
785

<210> SEQ ID NO 2
<211> LENGTH: 13
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<223> OTHER INFORMATION: SMOi1-1
<220> FEATURE:
<221> NAME/KEY: MISC_FEATURE
<222> LOCATION: (1)..(1)
<223> OTHER INFORMATION: wherein THR at position 1 optionally is
      palmitoylated

<400> SEQUENCE: 2

Thr Phe Val Ala Asp Trp Arg Asn Ser Asn Arg Tyr Pro
1               5                   10

<210> SEQ ID NO 3
<211> LENGTH: 25
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<223> OTHER INFORMATION: SMOi2-1
<220> FEATURE:
<221> NAME/KEY: MISC_FEATURE
<222> LOCATION: (1)..(1)
<223> OTHER INFORMATION: wherein LEU at position 1 optionally is
      palmitoylated

<400> SEQUENCE: 3

Leu Thr Tyr Ala Trp His Thr Ser Phe Lys Ala Leu Gly Thr Thr Tyr
1               5                   10                  15

Gln Pro Leu Ser Gly Lys Tyr Ser Tyr
            20                  25

<210> SEQ ID NO 4
<211> LENGTH: 31
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<223> OTHER INFORMATION: SMOi3-1
<220> FEATURE:
<221> NAME/KEY: MISC_FEATURE
<222> LOCATION: (1)..(1)
<223> OTHER INFORMATION: wherein ARG at position 1 optionally is
      palmitoylated

<400> SEQUENCE: 4

Arg Gly Val Met Thr Leu Phe Ser Ile Lys Ser Asn His Pro Gly Leu
1               5                   10                  15

Leu Ser Glu Lys Ala Ala Ser Lys Ile Asn Glu Thr Met Leu Arg
            20                  25                  30

<210> SEQ ID NO 5
<211> LENGTH: 6
<212> TYPE: PRT
<213> ORGANISM: Artificial Sequence
```

```
<220> FEATURE:
<223> OTHER INFORMATION: Synthetic Polypeptide
<220> FEATURE:
<221> NAME/KEY: MISC_FEATURE
<223> OTHER INFORMATION: C-term of i3

<400> SEQUENCE: 5

Leu Leu Ser Glu Lys Ala
1               5

<210> SEQ ID NO 6
<211> LENGTH: 8
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<223> OTHER INFORMATION: N-term of i3

<400> SEQUENCE: 6

Leu Phe Ser Ile Lys Ser Asn His
1               5

<210> SEQ ID NO 7
<211> LENGTH: 6
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<223> OTHER INFORMATION: C-term of i2

<400> SEQUENCE: 7

Gly Thr Thr Tyr Gln Pro
1               5

<210> SEQ ID NO 8
<211> LENGTH: 9
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<223> OTHER INFORMATION: N-term of i2

<400> SEQUENCE: 8

Tyr Ala Trp His Thr Ser Phe Lys Ala
1               5

<210> SEQ ID NO 9
<211> LENGTH: 21
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<223> OTHER INFORMATION: SMO-i3-2
<220> FEATURE:
<221> NAME/KEY: MISC_FEATURE
<223> OTHER INFORMATION: wherein ARG at position 1 optionally is
      palmitoylated

<400> SEQUENCE: 9

Arg Gly Val Met Thr Leu Phe Ser Ile Lys Ser Asn His Pro Gly Leu
1               5                   10                  15

Leu Ser Glu Lys Ala
```

20

<210> SEQ ID NO 10
<211> LENGTH: 26
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<223> OTHER INFORMATION: SMOi3-4
<220> FEATURE:
<221> NAME/KEY: MISC_FEATURE
<222> LOCATION: (1)..(1)
<223> OTHER INFORMATION: wherein LEU at position 1 optionally is
      palmitoylated

<400> SEQUENCE: 10

Leu Phe Ser Ile Lys Ser Asn His Pro Gly Leu Leu Ser Glu Lys Ala
1               5                   10                  15

Ala Ser Lys Ile Asn Glu Thr Met Leu Arg
            20                  25

<210> SEQ ID NO 11
<211> LENGTH: 31
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<223> OTHER INFORMATION: SMOi3-5-K

<400> SEQUENCE: 11

Arg Gly Val Met Thr Leu Phe Ser Ile Lys Ser Asn His Pro Gly Leu
1               5                   10                  15

Leu Ser Glu Lys Ala Ala Ser Lys Ile Asn Glu Thr Met Leu Arg
            20                  25                  30

<210> SEQ ID NO 12
<211> LENGTH: 16
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<223> OTHER INFORMATION: SMO-i3-6-K

<400> SEQUENCE: 12

Leu Leu Ser Glu Lys Ala Ala Ser Lys Ile Asn Glu Thr Met Leu Arg
1               5                   10                  15

<210> SEQ ID NO 13
<211> LENGTH: 26
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<223> OTHER INFORMATION: SMOi3-7-K

<400> SEQUENCE: 13

Leu Phe Ser Ile Lys Ser Asn His Pro Gly Leu Leu Ser Glu Lys Ala
1               5                   10                  15

Ala Ser Lys Ile Asn Glu Thr Met Leu Arg
            20                  25

```
<210> SEQ ID NO 14
<211> LENGTH: 18
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<223> OTHER INFORMATION: SMO-i3-8
<220> FEATURE:
<221> NAME/KEY: MISC_FEATURE
<222> LOCATION: (1)..(1)
<223> OTHER INFORMATION: wherein ARG at position 1 optionally is
      palmitoylated

<400> SEQUENCE: 14

Arg Gly Val Met Thr Leu Phe Ser Ile Lys Ser Asn His Pro Gly Leu
1               5                   10                  15

Leu Ser

<210> SEQ ID NO 15
<211> LENGTH: 13
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<223> OTHER INFORMATION: SMO-i3-10
<220> FEATURE:
<221> NAME/KEY: MISC_FEATURE
<222> LOCATION: (1)..(1)
<223> OTHER INFORMATION: wherein ARG at position 1 optionally is
      palmitoylated

<400> SEQUENCE: 15

Arg Gly Val Met Thr Leu Phe Ser Ile Lys Ser Asn His
1               5                   10

<210> SEQ ID NO 16
<211> LENGTH: 14
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<223> OTHER INFORMATION: SMOi3-12-K

<400> SEQUENCE: 16

Ser Glu Lys Ala Ala Ser Lys Ile Asn Glu Thr Met Leu Arg
1               5                   10

<210> SEQ ID NO 17
<211> LENGTH: 25
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<223> OTHER INFORMATION: SMO i2-2
<220> FEATURE:
<221> NAME/KEY: MISC_FEATURE
<222> LOCATION: (1)..(1)
<223> OTHER INFORMATION: wherein LEU at position 1 optionally is
      palmitoylated

<400> SEQUENCE: 17

Leu Thr Tyr Ala Trp His Thr Ser Phe Lys Ala Leu Gly Thr Thr Tyr
1               5                   10                  15
```

```
Gln Pro Leu Ser Gly Lys Thr Ser Tyr
            20                  25

<210> SEQ ID NO 18
<211> LENGTH: 21
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<223> OTHER INFORMATION: SMO i2-3
<220> FEATURE:
<221> NAME/KEY: MISC_FEATURE
<222> LOCATION: (1)..(1)
<223> OTHER INFORMATION: wherein the LEU at position 1 optionally is
      palmitoylated

<400> SEQUENCE: 18

Leu Thr Tyr Ala Trp His Thr Ser Phe Lys Ala Leu Gly Thr Thr Tyr
1               5                   10                  15

Gln Pro Leu Ser Gly
            20

<210> SEQ ID NO 19
<211> LENGTH: 25
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<223> OTHER INFORMATION: SMOi2-4-K
<220> FEATURE:
<221> NAME/KEY: MISC_FEATURE
<222> LOCATION: (1)..(1)
<223> OTHER INFORMATION: wherein LEU at position 1 optionally is
      acetylated

<400> SEQUENCE: 19

Leu Thr Tyr Ala Trp His Thr Ser Phe Lys Ala Leu Gly Thr Thr Tyr
1               5                   10                  15

Gln Pro Leu Ser Gly Lys Thr Ser Tyr
            20                  25

<210> SEQ ID NO 20
<211> LENGTH: 23
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<223> OTHER INFORMATION: SMO i2-5-K
<220> FEATURE:
<221> NAME/KEY: MISC_FEATURE
<222> LOCATION: (1)..(1)
<223> OTHER INFORMATION: wherein the TYR at position 1 optionally is
      acetylated

<400> SEQUENCE: 20

Tyr Ala Trp His Thr Ser Phe Lys Ala Leu Gly Thr Thr Tyr Gln Pro
1               5                   10                  15

Leu Ser Gly Lys Thr Ser Tyr
            20

<210> SEQ ID NO 21
<211> LENGTH: 18
<212> TYPE: PRT
```

```
<213> ORGANISM: Artificial Sequence
<220> FEATURE:
<223> OTHER INFORMATION: Synthetic Polypeptide
<220> FEATURE:
<221> NAME/KEY: MISC_FEATURE
<223> OTHER INFORMATION: SMO i2-6
<220> FEATURE:
<221> NAME/KEY: MISC_FEATURE
<222> LOCATION: (1)..(1)
<223> OTHER INFORMATION: wherein the LEU at position 1 optionally is
      palmitoylated

<400> SEQUENCE: 21

Leu Thr Tyr Ala Trp His Thr Ser Phe Lys Ala Leu Gly Thr Thr Tyr
1               5                   10                  15

Gln Pro

<210> SEQ ID NO 22
<211> LENGTH: 13
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<223> OTHER INFORMATION: SMO i2-7-K

<400> SEQUENCE: 22

Gly Thr Thr Tyr Gln Pro Leu Ser Gly Lys Thr Ser Tyr
1               5                   10

<210> SEQ ID NO 23
<211> LENGTH: 12
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<223> OTHER INFORMATION: SMO i2-8
<220> FEATURE:
<221> NAME/KEY: MISC_FEATURE
<222> LOCATION: (1)..(1)
<223> OTHER INFORMATION: wherein the LEU at position 1 optionally is
      palmitoylated

<400> SEQUENCE: 23

Leu Thr Tyr Ala Trp His Thr Ser Phe Lys Ala Leu
1               5                   10

<210> SEQ ID NO 24
<211> LENGTH: 12
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<223> OTHER INFORMATION: SMO i2-9
<220> FEATURE:
<221> NAME/KEY: MISC_FEATURE
<222> LOCATION: (1)..(1)
<223> OTHER INFORMATION: wherein the LEU at position 1 optionally is
      acetylated

<400> SEQUENCE: 24

Leu Thr Tyr Ala Trp His Thr Ser Phe Lys Ala Leu
1               5                   10

<210> SEQ ID NO 25
<211> LENGTH: 11
```

```
-continued

<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<223> OTHER INFORMATION: SMO i2-10
<220> FEATURE:
<221> NAME/KEY: MISC_FEATURE
<222> LOCATION: (1)..(1)
<223> OTHER INFORMATION: wherein the THR at position 1 optionally is
      palmitoylated

<400> SEQUENCE: 25

Thr Tyr Ala Trp His Thr Ser Phe Lys Ala Leu
1               5                   10

<210> SEQ ID NO 26
<211> LENGTH: 11
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<223> OTHER INFORMATION: SMO i2-11
<220> FEATURE:
<221> NAME/KEY: MISC_FEATURE
<222> LOCATION: (1)..(1)
<223> OTHER INFORMATION: wherein the LEU at position 1 optionally is
      palmitoylated

<400> SEQUENCE: 26

Leu Thr Tyr Ala Trp His Thr Ser Phe Lys Ala
1               5                   10

<210> SEQ ID NO 27
<211> LENGTH: 10
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<223> OTHER INFORMATION: SMO i2-12
<220> FEATURE:
<221> NAME/KEY: MISC_FEATURE
<222> LOCATION: (1)..(1)
<223> OTHER INFORMATION: wherein the LEU at position 1 optionally is
      palmitoylated

<400> SEQUENCE: 27

Leu Thr Tyr Ala Trp His Thr Ser Phe Lys
1               5                   10

<210> SEQ ID NO 28
<211> LENGTH: 10
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<223> OTHER INFORMATION: SMO i2-13
<220> FEATURE:
<221> NAME/KEY: MISC_FEATURE
<222> LOCATION: (1)..(1)
<223> OTHER INFORMATION: wherein the THR at position 1 optionally is
      acetylated

<400> SEQUENCE: 28

Thr Tyr Ala Trp His Thr Ser Phe Lys Ala
1               5                   10
```

```
<210> SEQ ID NO 29
<211> LENGTH: 25
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<223> OTHER INFORMATION: SMOi2-23-K (i2-2 doubly palmitylated)
<220> FEATURE:
<221> NAME/KEY: MISC_FEATURE
<222> LOCATION: (1)..(1)
<223> OTHER INFORMATION: wherein the LEU at position 1 optionally is
      palmitoylated

<400> SEQUENCE: 29

Leu Thr Tyr Ala Trp His Thr Ser Phe Lys Ala Leu Gly Thr Thr Tyr
1               5                   10                  15

Gln Pro Leu Ser Gly Lys Thr Ser Tyr
            20                  25

<210> SEQ ID NO 30
<211> LENGTH: 12
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<223> OTHER INFORMATION: SMOi2-24
<220> FEATURE:
<221> NAME/KEY: MISC_FEATURE
<223> OTHER INFORMATION: wherein each amino acid is the D isomer
<220> FEATURE:
<221> NAME/KEY: MISC_FEATURE
<222> LOCATION: (1)..(1)
<223> OTHER INFORMATION: wherein LEU at position 1 optionally is
      palmitoylated

<400> SEQUENCE: 30

Leu Thr Tyr Ala Trp His Thr Ser Phe Lys Ala Leu
1               5                   10

<210> SEQ ID NO 31
<211> LENGTH: 12
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<223> OTHER INFORMATION: SMOi2-25
<220> FEATURE:
<221> NAME/KEY: MISC_FEATURE
<223> OTHER INFORMATION: wherein each amino acid is the D isomer
<220> FEATURE:
<221> NAME/KEY: MISC_FEATURE
<222> LOCATION: (1)..(1)
<223> OTHER INFORMATION: wherein the LEU at position 1 optionally is
      acetylated

<400> SEQUENCE: 31

Leu Thr Tyr Ala Trp His Thr Ser Phe Lys Ala Leu
1               5                   10

<210> SEQ ID NO 32
<211> LENGTH: 12
<212> TYPE: PRT
<213> ORGANISM: Artificial Sequence
<220> FEATURE:
<223> OTHER INFORMATION: Synthetic Polypeptide
```

```
<220> FEATURE:
<221> NAME/KEY: MISC_FEATURE
<223> OTHER INFORMATION: SMOi2-26
<220> FEATURE:
<221> NAME/KEY: MISC_FEATURE
<222> LOCATION: (1)..(1)
<223> OTHER INFORMATION: wherein the LEU at position 1 optionally
      comprises myristate

<400> SEQUENCE: 32

Leu Thr Tyr Ala Trp His Thr Ser Phe Lys Ala Leu
1               5                   10

<210> SEQ ID NO 33
<211> LENGTH: 10
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<223> OTHER INFORMATION: Forward seq of i2-20

<400> SEQUENCE: 33

Leu Thr Tyr Ala Trp His Thr Ser Phe Lys
1               5                   10

<210> SEQ ID NO 34
<211> LENGTH: 12
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<223> OTHER INFORMATION: SMO i2-16-K retroinverso of SMOi2-8
<220> FEATURE:
<221> NAME/KEY: MISC_FEATURE
<223> OTHER INFORMATION: SMO i2-16-K retroinverso of SMOi2-8
<220> FEATURE:
<221> NAME/KEY: MISC_FEATURE
<223> OTHER INFORMATION: wherein each of the amino acids is the D isomer
<220> FEATURE:
<221> NAME/KEY: MISC_FEATURE
<222> LOCATION: (1)..(1)
<223> OTHER INFORMATION: wherein the LEU at position 1 optionally is
      acetylated

<400> SEQUENCE: 34

Leu Ala Lys Phe Ser Thr His Trp Ala Tyr Thr Leu
1               5                   10

<210> SEQ ID NO 35
<211> LENGTH: 11
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<223> OTHER INFORMATION: SMO i2-17-K retroinverso of SMOi2-11
<220> FEATURE:
<221> NAME/KEY: MISC_FEATURE
<223> OTHER INFORMATION: wherein each of the amino acids is the D isomer
<220> FEATURE:
<221> NAME/KEY: MISC_FEATURE
<222> LOCATION: (1)..(1)
<223> OTHER INFORMATION: wherein the ALA at position 1 optionally is
      acetylated

<400> SEQUENCE: 35

Ala Lys Phe Ser Thr His Trp Ala Tyr Thr Leu
1               5                   10
```

```
<210> SEQ ID NO 36
<211> LENGTH: 10
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<223> OTHER INFORMATION: SMOi2-20-K
<220> FEATURE:
<221> NAME/KEY: MISC_FEATURE
<223> OTHER INFORMATION: wherein each of the amino acids is the D isomer
<220> FEATURE:
<221> NAME/KEY: MISC_FEATURE
<222> LOCATION: (1)..(1)
<223> OTHER INFORMATION: wherein the LYS at position 1 optionally is
      acetylated

<400> SEQUENCE: 36

Lys Phe Ser Thr His Trp Ala Tyr Thr Leu
1               5                   10

<210> SEQ ID NO 37
<211> LENGTH: 11
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<223> OTHER INFORMATION: SMOi2-22
<220> FEATURE:
<221> NAME/KEY: MISC_FEATURE
<223> OTHER INFORMATION: wherein each of the amino acids is the D isomer

<400> SEQUENCE: 37

Ala Lys Phe Ser Thr His Trp Ala Tyr Thr Leu
1               5                   10

<210> SEQ ID NO 38
<211> LENGTH: 23
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<223> OTHER INFORMATION: SMOi2-1
<220> FEATURE:
<221> NAME/KEY: MISC_FEATURE
<222> LOCATION: (1)..(1)
<223> OTHER INFORMATION: wherein THR at position 1 optionally is
      palmitoylated
<220> FEATURE:
<221> NAME/KEY: MISC_FEATURE
<222> LOCATION: (4)..(4)
<223> OTHER INFORMATION: wherein X at position 4 is Y, F, or
      benzoylphenalanine (BPA)

<400> SEQUENCE: 38

Thr Tyr Ala Xaa His Thr Ser Phe Lys Ala Leu Gly Thr Thr Tyr Gln
1               5                   10                  15

Pro Leu Ser Gly Lys Thr Ser
            20

<210> SEQ ID NO 39
<211> LENGTH: 25
<212> TYPE: PRT
<213> ORGANISM: Artificial Sequence
<220> FEATURE:
<223> OTHER INFORMATION: Synthetic Polypeptide
```

```
<220> FEATURE:
<221> NAME/KEY: MISC_FEATURE
<223> OTHER INFORMATION: Generic SMOi2-2
<220> FEATURE:
<221> NAME/KEY: MISC_FEATURE
<223> OTHER INFORMATION: wherein LEU at position 1 optionally is
      palmitoylated
<220> FEATURE:
<221> NAME/KEY: MISC_FEATURE
<222> LOCATION: (5)..(5)
<223> OTHER INFORMATION: wherein X at position 5 is Y, F, or
      4-benzoylphenalalanine (BPA)

<400> SEQUENCE: 39

Leu Thr Tyr Ala Xaa His Thr Ser Phe Lys Ala Leu Gly Thr Thr Tyr
1               5                   10                  15

Gln Pro Leu Ser Gly Lys Thr Ser Tyr
            20                  25

<210> SEQ ID NO 40
<211> LENGTH: 21
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<223> OTHER INFORMATION: Generic SMOi2-3
<220> FEATURE:
<221> NAME/KEY: MISC_FEATURE
<222> LOCATION: (1)..(1)
<223> OTHER INFORMATION: wherein the LEU at position 1 optionally is
      palmitoylated
<220> FEATURE:
<221> NAME/KEY: MISC_FEATURE
<222> LOCATION: (5)..(5)
<223> OTHER INFORMATION: wherein X at position 5 is Y, F, or
      4-benzoylphenalalanine (BPA)

<400> SEQUENCE: 40

Leu Thr Tyr Ala Xaa His Thr Ser Phe Lys Ala Leu Gly Thr Thr Tyr
1               5                   10                  15

Gln Pro Leu Ser Gly
            20

<210> SEQ ID NO 41
<211> LENGTH: 25
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<223> OTHER INFORMATION: Generic SMOi2-4
<220> FEATURE:
<221> NAME/KEY: MISC_FEATURE
<222> LOCATION: (1)..(1)
<223> OTHER INFORMATION: wherein the LEU at position 1 optionally
      comprises an acetyl residue
<220> FEATURE:
<221> NAME/KEY: MISC_FEATURE
<222> LOCATION: (5)..(5)
<223> OTHER INFORMATION: wherein X at position 5 is Y, F, or
      4-benzoylphenalalanine

<400> SEQUENCE: 41

Leu Thr Tyr Ala Xaa His Thr Ser Phe Lys Ala Leu Gly Thr Thr Tyr
1               5                   10                  15

Gln Pro Leu Ser Gly Lys Thr Ser Tyr
            20                  25
```

```
<210> SEQ ID NO 42
<211> LENGTH: 23
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<223> OTHER INFORMATION: Generic SMOi2-5
<220> FEATURE:
<221> NAME/KEY: MISC_FEATURE
<222> LOCATION: (1)..(1)
<223> OTHER INFORMATION: wherein the TYR at position 1 optionally is
      acetylated
<220> FEATURE:
<221> NAME/KEY: MISC_FEATURE
<222> LOCATION: (3)..(3)
<223> OTHER INFORMATION: wherein X at position 3 is Y, F, or
      4-benzoylphenalalanine

<400> SEQUENCE: 42

Tyr Ala Xaa His Thr Ser Phe Lys Ala Leu Gly Thr Thr Tyr Gln Pro
1               5                   10                  15

Leu Ser Gly Lys Thr Ser Tyr
            20

<210> SEQ ID NO 43
<211> LENGTH: 18
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<223> OTHER INFORMATION: Generic SMOi2-6
<220> FEATURE:
<221> NAME/KEY: MISC_FEATURE
<222> LOCATION: (1)..(1)
<223> OTHER INFORMATION: wherein the LEU at position 1 is palmitoylated
<220> FEATURE:
<221> NAME/KEY: MISC_FEATURE
<222> LOCATION: (5)..(5)
<223> OTHER INFORMATION: wherein X at position 5 is Y, F, or
      4-benzoylphenalalanine

<400> SEQUENCE: 43

Leu Thr Tyr Ala Xaa His Thr Ser Phe Lys Ala Leu Gly Thr Thr Tyr
1               5                   10                  15

Gln Pro

<210> SEQ ID NO 44
<211> LENGTH: 12
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<223> OTHER INFORMATION: Generic SMOi2-8
<220> FEATURE:
<221> NAME/KEY: MISC_FEATURE
<222> LOCATION: (1)..(1)
<223> OTHER INFORMATION: wherein the LEU at position 1 is palmitoylated
<220> FEATURE:
<221> NAME/KEY: MISC_FEATURE
<222> LOCATION: (5)..(5)
<223> OTHER INFORMATION: wherein X at position 5 is Y, F, or
      4-benzoylphenalalanine

<400> SEQUENCE: 44

Leu Thr Tyr Ala Xaa His Thr Ser Phe Lys Ala Leu
1               5                   10
```

```
<210> SEQ ID NO 45
<211> LENGTH: 11
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<223> OTHER INFORMATION: Generic SMOi2-10
<220> FEATURE:
<221> NAME/KEY: MISC_FEATURE
<222> LOCATION: (1)..(1)
<223> OTHER INFORMATION: wherein the T at position 1 optionally is
      palmitoylated
<220> FEATURE:
<221> NAME/KEY: MISC_FEATURE
<222> LOCATION: (4)..(4)
<223> OTHER INFORMATION: wherein X at position 4 is Y, F, or
      4-benzoylphenalalanine

<400> SEQUENCE: 45

Thr Tyr Ala Xaa His Thr Ser Phe Lys Ala Leu
1               5                   10

<210> SEQ ID NO 46
<211> LENGTH: 11
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<223> OTHER INFORMATION: Generic SMOi2-11
<220> FEATURE:
<221> NAME/KEY: MISC_FEATURE
<222> LOCATION: (1)..(1)
<223> OTHER INFORMATION: wherein the LEU at position 1 optionally is
      palmitoylated
<220> FEATURE:
<221> NAME/KEY: MISC_FEATURE
<222> LOCATION: (5)..(5)
<223> OTHER INFORMATION: wherein X at position 5 is Y, F, or
      4-benzoylphenalalanine

<400> SEQUENCE: 46

Leu Thr Tyr Ala Xaa His Thr Ser Phe Lys Ala
1               5                   10

<210> SEQ ID NO 47
<211> LENGTH: 10
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<223> OTHER INFORMATION: Generic SMOi2-12
<220> FEATURE:
<221> NAME/KEY: MISC_FEATURE
<222> LOCATION: (1)..(1)
<223> OTHER INFORMATION: wherein the THR at position 1 optionally is
      palmitoylated
<220> FEATURE:
<221> NAME/KEY: MISC_FEATURE
<222> LOCATION: (4)..(4)
<223> OTHER INFORMATION: wherein X at position 4  is Y, F, or
      4-benzoylphenalalanine

<400> SEQUENCE: 47

Thr Tyr Ala Xaa His Thr Ser Phe Lys Ala
1               5                   10

<210> SEQ ID NO 48
```

```
<211> LENGTH: 10
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<223> OTHER INFORMATION: Generic SMOi2-13
<220> FEATURE:
<221> NAME/KEY: MISC_FEATURE
<222> LOCATION: (1)..(1)
<223> OTHER INFORMATION: wherein the THR at position 1 optionally is
      acetylated
<220> FEATURE:
<221> NAME/KEY: MISC_FEATURE
<222> LOCATION: (4)..(4)
<223> OTHER INFORMATION: wherein X at position 4 is Y, F, or
      4-benzoylphenalalanine

<400> SEQUENCE: 48

Thr Tyr Ala Xaa His Thr Ser Phe Lys Ala
1               5                   10

<210> SEQ ID NO 49
<211> LENGTH: 12
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<223> OTHER INFORMATION: Generic SMOi2-16
<220> FEATURE:
<221> NAME/KEY: MISC_FEATURE
<223> OTHER INFORMATION: wherein each of the amino acids is the D isomer
<220> FEATURE:
<221> NAME/KEY: MISC_FEATURE
<222> LOCATION: (8)..(8)
<223> OTHER INFORMATION: wherein X at position 8 is Y, F, or
      4-benzoylphenalalanine

<400> SEQUENCE: 49

Leu Ala Lys Phe Ser Thr His Xaa Ala Tyr Thr Leu
1               5                   10

<210> SEQ ID NO 50
<211> LENGTH: 11
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<223> OTHER INFORMATION: Generic SMOi2-17
<220> FEATURE:
<221> NAME/KEY: MISC_FEATURE
<223> OTHER INFORMATION: wherein each of the amino acids is the D isomer
<220> FEATURE:
<221> NAME/KEY: MISC_FEATURE
<222> LOCATION: (1)..(1)
<223> OTHER INFORMATION: wherein the ALA at position 1 optionally is
      acetylated
<220> FEATURE:
<221> NAME/KEY: MISC_FEATURE
<222> LOCATION: (7)..(7)
<223> OTHER INFORMATION: wherein X at position 7 is Y, F, or
      4-benzoylphenalalanine (BPA)

<400> SEQUENCE: 50

Ala Lys Phe Ser Thr His Xaa Ala Tyr Thr Leu
1               5                   10

<210> SEQ ID NO 51
<211> LENGTH: 10
```

```
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<223> OTHER INFORMATION: Generic SMOi2-20
<220> FEATURE:
<221> NAME/KEY: MISC_FEATURE
<223> OTHER INFORMATION: wherein each of the amino acids is the D isomer
<220> FEATURE:
<221> NAME/KEY: MISC_FEATURE
<222> LOCATION: (1)..(1)
<223> OTHER INFORMATION: wherein the LYS at position 1 optionally is
      acetylated
<220> FEATURE:
<221> NAME/KEY: MISC_FEATURE
<222> LOCATION: (6)..(6)
<223> OTHER INFORMATION: wherein X at position 6 is Y, F, or
      4-benzoylphenalalanine (BPA)

<400> SEQUENCE: 51

Lys Phe Ser Thr His Xaa Ala Tyr Thr Leu
1               5                   10

<210> SEQ ID NO 52
<211> LENGTH: 11
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<223> OTHER INFORMATION: Generic SMOi2-22
<220> FEATURE:
<221> NAME/KEY: MISC_FEATURE
<223> OTHER INFORMATION: wherein each of the amino acids is the D isomer
<220> FEATURE:
<221> NAME/KEY: MISC_FEATURE
<222> LOCATION: (7)..(7)
<223> OTHER INFORMATION: wherein X at position 7 is Y, F, or
      4-benzoylphenalalanine (BPA)

<400> SEQUENCE: 52

Ala Lys Phe Ser Thr His Xaa Ala Tyr Thr Leu
1               5                   10

<210> SEQ ID NO 53
<211> LENGTH: 25
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<223> OTHER INFORMATION: Generic SMOi2-23
<220> FEATURE:
<221> NAME/KEY: MISC_FEATURE
<222> LOCATION: (1)..(1)
<223> OTHER INFORMATION: wherein LEU at position 1 optionally is
      palmitoylated
<220> FEATURE:
<221> NAME/KEY: MISC_FEATURE
<222> LOCATION: (5)..(5)
<223> OTHER INFORMATION: wherein X at position 5 is Y, F, or
      4-benzoylphenalalanine (BPA)

<400> SEQUENCE: 53

Leu Thr Tyr Ala Xaa His Thr Ser Phe Lys Ala Leu Gly Thr Thr Tyr
1               5                   10                  15

Gln Pro Leu Ser Gly Lys Thr Ser Tyr
            20                  25
```

```
<210> SEQ ID NO 54
<211> LENGTH: 12
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<223> OTHER INFORMATION: SMOi2-18
<220> FEATURE:
<221> NAME/KEY: MISC_FEATURE
<222> LOCATION: (1)..(1)
<223> OTHER INFORMATION: wherein the LEU at position 1 optionally is
      palmitoylated
<220> FEATURE:
<221> NAME/KEY: MISC_FEATURE
<222> LOCATION: (5)..(5)
<223> OTHER INFORMATION: wherein X at position 5 is BPA

<400> SEQUENCE: 54

Leu Thr Tyr Ala Xaa His Thr Ser Phe Lys Ala Leu
1               5                   10

<210> SEQ ID NO 55
<211> LENGTH: 17
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<223> OTHER INFORMATION: SMOi2-14

<400> SEQUENCE: 55

Val Trp Phe Val Val Leu Thr Tyr Ala Trp His Thr Ser Phe Lys Ala
1               5                   10                  15

Leu

<210> SEQ ID NO 56
<211> LENGTH: 16
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<223> OTHER INFORMATION: SMOi2-15

<400> SEQUENCE: 56

Trp Phe Val Val Leu Thr Tyr Ala Trp His Thr Ser Phe Lys Ala Leu
1               5                   10                  15

<210> SEQ ID NO 57
<211> LENGTH: 12
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<223> OTHER INFORMATION: SMOi2-24
<220> FEATURE:
<221> NAME/KEY: MISC_FEATURE
<223> OTHER INFORMATION: wherein each amino acid is the D isomer
<220> FEATURE:
<221> NAME/KEY: MISC_FEATURE
<222> LOCATION: (1)..(1)
<223> OTHER INFORMATION: wherein the LEU at position 1 optionally is
      palmitoylated
<220> FEATURE:
<221> NAME/KEY: MISC_FEATURE
<222> LOCATION: (5)..(5)
<223> OTHER INFORMATION: wherein X at position 5 is Y, F, or
```

-continued

```
      4-benzoylphenalalanine (BPA)

<400> SEQUENCE: 57

Leu Thr Tyr Ala Xaa His Thr Ser Phe Lys Ala Leu
1               5                   10

<210> SEQ ID NO 58
<211> LENGTH: 12
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<223> OTHER INFORMATION: SMOi2-25
<220> FEATURE:
<221> NAME/KEY: MISC_FEATURE
<223> OTHER INFORMATION: wherein each of the amino acids is the D isomer
<220> FEATURE:
<221> NAME/KEY: MISC_FEATURE
<222> LOCATION: (1)..(1)
<223> OTHER INFORMATION: wherein the LEU at position 1 optionally is
      acetylated
<220> FEATURE:
<221> NAME/KEY: MISC_FEATURE
<222> LOCATION: (5)..(5)
<223> OTHER INFORMATION: wherein X at position 5 is Y, F, or
      4-benzoylphenalalanine (BPA)

<400> SEQUENCE: 58

Leu Thr Tyr Ala Xaa His Thr Ser Phe Lys Ala Leu
1               5                   10

<210> SEQ ID NO 59
<211> LENGTH: 12
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<223> OTHER INFORMATION: SMOi2-26
<220> FEATURE:
<221> NAME/KEY: MISC_FEATURE
<222> LOCATION: (1)..(1)
<223> OTHER INFORMATION: wherein the LEU at position 1 optionally is
      myristoylated
<220> FEATURE:
<221> NAME/KEY: MISC_FEATURE
<222> LOCATION: (5)..(5)
<223> OTHER INFORMATION: wherein X at position 5 is Y, F, or
      4-benzoylphenalalanine (BPA)

<400> SEQUENCE: 59

Leu Thr Tyr Ala Xaa His Thr Ser Phe Lys Ala Leu
1               5                   10

<210> SEQ ID NO 60
<211> LENGTH: 32
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<223> OTHER INFORMATION: Generic SMOi3-5
<220> FEATURE:
<221> NAME/KEY: MISC_FEATURE
<222> LOCATION: (32)..(32)
<223> OTHER INFORMATION: wherein X at position 32 is K, C, homoCys, Orn,
      diaminobutyric acid (DBA), or diaminopropaneic acid (DPA)
<220> FEATURE:
<221> NAME/KEY: MISC_FEATURE
<222> LOCATION: (32)..(32)
```

```
<223> OTHER INFORMATION: wherein X at position 32 is optionally
      palmitoylated

<400> SEQUENCE: 60

Arg Gly Val Met Thr Leu Phe Ser Ile Lys Ser Asn His Pro Gly Leu
1               5                   10                  15

Leu Ser Glu Lys Ala Ala Ser Lys Ile Asn Glu Thr Met Leu Arg Xaa
            20                  25                  30

<210> SEQ ID NO 61
<211> LENGTH: 17
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<223> OTHER INFORMATION: Generic SMOi3-6
<220> FEATURE:
<221> NAME/KEY: MISC_FEATURE
<222> LOCATION: (17)..(17)
<223> OTHER INFORMATION: wherein X at position 17 is K, C, homoCys, Orn,
      diaminobutyric acid (DBA), or diaminopropanoic acid (DPA)
<220> FEATURE:
<221> NAME/KEY: MISC_FEATURE
<222> LOCATION: (17)..(17)
<223> OTHER INFORMATION: wherein X at position 17 optionally is
      palmitoylated

<400> SEQUENCE: 61

Leu Leu Ser Glu Lys Ala Ala Ser Lys Ile Asn Glu Thr Met Leu Arg
1               5                   10                  15

Xaa

<210> SEQ ID NO 62
<211> LENGTH: 27
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<223> OTHER INFORMATION: Generic SMOi3-7
<220> FEATURE:
<221> NAME/KEY: MISC_FEATURE
<222> LOCATION: (27)..(27)
<223> OTHER INFORMATION: wherein X at position 27 is K, C, homoCys, Orn,
      diaminobutyric acid (DBA), or diaminopropanoic acid (DPA)
<220> FEATURE:
<221> NAME/KEY: MISC_FEATURE
<222> LOCATION: (27)..(27)
<223> OTHER INFORMATION: wherein X at position 27 optionally is
      palmitoylated

<400> SEQUENCE: 62

Leu Phe Ser Ile Lys Ser Asn His Pro Gly Leu Leu Ser Glu Lys Ala
1               5                   10                  15

Ala Ser Lys Ile Asn Glu Thr Met Leu Arg Xaa
            20                  25

<210> SEQ ID NO 63
<211> LENGTH: 15
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<223> OTHER INFORMATION: SMOi3-12
<220> FEATURE:
<221> NAME/KEY: MISC_FEATURE
```

```
<222> LOCATION: (15)..(15)
<223> OTHER INFORMATION: wherein X at position 15 is K, C, homoCys, Orn,
      diaminobutyric acid (DBA), or diaminopropanoic acid (DPA), wherein
      X at position 15 optionally is palmitoylated

<400> SEQUENCE: 63

Ser Glu Lys Ala Ala Ser Lys Ile Asn Glu Thr Met Leu Arg Xaa
1               5                   10                  15

<210> SEQ ID NO 64
<211> LENGTH: 26
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<223> OTHER INFORMATION: SMOi2-4
<220> FEATURE:
<221> NAME/KEY: MISC_FEATURE
<222> LOCATION: (1)..(1)
<223> OTHER INFORMATION: wherein LEU at position 1 comprises acetate
<220> FEATURE:
<221> NAME/KEY: MISC_FEATURE
<222> LOCATION: (26)..(26)
<223> OTHER INFORMATION: wherein X at position 26 is K, C, homoCys, Orn,
      diaminobutyric acid (DBA), or diaminopropanoic acid (DPA)
<220> FEATURE:
<221> NAME/KEY: MISC_FEATURE
<222> LOCATION: (26)..(26)
<223> OTHER INFORMATION: wherein X at position 26 optionally is
      palmitoylated

<400> SEQUENCE: 64

Leu Thr Tyr Ala Trp His Thr Ser Phe Lys Ala Leu Gly Thr Thr Tyr
1               5                   10                  15

Gln Pro Leu Ser Gly Lys Thr Ser Tyr Xaa
            20                  25

<210> SEQ ID NO 65
<211> LENGTH: 24
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<223> OTHER INFORMATION: SMOi2-5
<220> FEATURE:
<221> NAME/KEY: MISC_FEATURE
<222> LOCATION: (1)..(1)
<223> OTHER INFORMATION: wherein TYR at position 1 comprises acetate
<220> FEATURE:
<221> NAME/KEY: MISC_FEATURE
<222> LOCATION: (24)..(24)
<223> OTHER INFORMATION: wherein X at position 24 is K, C, homoCys, Orn,
      diaminobutyric acid (DBA), or diaminopropanoic acid (DPA)
<220> FEATURE:
<221> NAME/KEY: MISC_FEATURE
<222> LOCATION: (24)..(24)
<223> OTHER INFORMATION: wherein X at position 24 optionally is
      palmitoylated

<400> SEQUENCE: 65

Tyr Ala Trp His Thr Ser Phe Lys Ala Leu Gly Thr Thr Tyr Gln Pro
1               5                   10                  15

Leu Ser Gly Lys Thr Ser Tyr Xaa
            20

<210> SEQ ID NO 66
<211> LENGTH: 14
<212> TYPE: PRT
```

```
<213> ORGANISM: Artificial Sequence
<220> FEATURE:
<223> OTHER INFORMATION: Synthetic Polypeptide
<220> FEATURE:
<221> NAME/KEY: MISC_FEATURE
<223> OTHER INFORMATION: SMOi2-7
<220> FEATURE:
<221> NAME/KEY: MISC_FEATURE
<222> LOCATION: (14)..(14)
<223> OTHER INFORMATION: wherein X at position 14 is K, C, homoCys, Orn,
      or diaminobutyric acid (DBA), or diaminopropanoic acid (DPA);
      wherein X at position 14 optionally is palmitoylated

<400> SEQUENCE: 66

Gly Thr Thr Tyr Gln Pro Leu Ser Gly Lys Thr Ser Tyr Xaa
1               5                   10

<210> SEQ ID NO 67
<211> LENGTH: 13
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<223> OTHER INFORMATION: SMOi2-16
<220> FEATURE:
<221> NAME/KEY: MISC_FEATURE
<223> OTHER INFORMATION: wherein each of the amino acids is the D isomer
<220> FEATURE:
<221> NAME/KEY: MISC_FEATURE
<222> LOCATION: (1)..(1)
<223> OTHER INFORMATION: wherein LEU at position 1 optionally is
      acetylated
<220> FEATURE:
<221> NAME/KEY: MISC_FEATURE
<222> LOCATION: (13)..(13)
<223> OTHER INFORMATION: wherein X at position 13 is K, C, homoCys, Orn,
      diaminobutyric acid (DBA), or diaminopropanoic acid (DPA)
<220> FEATURE:
<221> NAME/KEY: MISC_FEATURE
<222> LOCATION: (13)..(13)
<223> OTHER INFORMATION: wherein X at position 13 optionally is
      palmitoylated

<400> SEQUENCE: 67

Leu Ala Lys Phe Ser Thr His Trp Ala Tyr Thr Leu Xaa
1               5                   10

<210> SEQ ID NO 68
<211> LENGTH: 12
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<223> OTHER INFORMATION: SMOi2-17
<220> FEATURE:
<221> NAME/KEY: MISC_FEATURE
<223> OTHER INFORMATION: wherein each of the amino acids is the D isomer
<220> FEATURE:
<221> NAME/KEY: MISC_FEATURE
<222> LOCATION: (1)..(1)
<223> OTHER INFORMATION: wherein the ALA at position 1 optionally is
      acetylated
<220> FEATURE:
<221> NAME/KEY: MISC_FEATURE
<222> LOCATION: (12)..(12)
<223> OTHER INFORMATION: wherein X at position 12 is K, C, homoCys, Orn,
      diaminobutyric acid (DBA), or diaminopropanoic acid (DPA)
<220> FEATURE:
<221> NAME/KEY: MISC_FEATURE
<222> LOCATION: (12)..(12)
<223> OTHER INFORMATION: wherein X at position 12 optionally is
      palmitoylated
```

```
<400> SEQUENCE: 68

Ala Lys Phe Ser Thr His Trp Ala Tyr Thr Leu Xaa
1               5                   10

<210> SEQ ID NO 69
<211> LENGTH: 11
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<223> OTHER INFORMATION: SMOi2-20
<220> FEATURE:
<221> NAME/KEY: MISC_FEATURE
<223> OTHER INFORMATION: wherein each of the amino acids is the D isomer
<220> FEATURE:
<221> NAME/KEY: MISC_FEATURE
<222> LOCATION: (1)..(1)
<223> OTHER INFORMATION: wherein LYS at position 1 optionally is
      acetylated
<220> FEATURE:
<221> NAME/KEY: MISC_FEATURE
<222> LOCATION: (11)..(11)
<223> OTHER INFORMATION: wherein X at position 11 optionally is
      palmitoylated
<220> FEATURE:
<221> NAME/KEY: MISC_FEATURE
<222> LOCATION: (11)..(11)
<223> OTHER INFORMATION: wherein X at position 11 is K, C, homoCys, Orn,
      diaminobutyric acid (DBA), or diaminopropanoic acid (DPA)

<400> SEQUENCE: 69

Lys Phe Ser Thr His Trp Ala Tyr Thr Leu Xaa
1               5                   10

<210> SEQ ID NO 70
<211> LENGTH: 26
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<223> OTHER INFORMATION: SMOi2-23
<220> FEATURE:
<221> NAME/KEY: MISC_FEATURE
<222> LOCATION: (1)..(1)
<223> OTHER INFORMATION: wherein each of L at position 1 and X at
      position 26 optionally is palimitoylated
<220> FEATURE:
<221> NAME/KEY: MISC_FEATURE
<222> LOCATION: (26)..(26)
<223> OTHER INFORMATION: wherein X at position 26 is K, C, homoCys, Orn,
      diaminobutyric acid (DBA), or diaminopropanoic acid (DPA)
<220> FEATURE:
<221> NAME/KEY: MISC_FEATURE
<222> LOCATION: (26)..(26)
<223> OTHER INFORMATION: wherein each of L at position 1 and X at
      position 26 optionally is palimitoylated

<400> SEQUENCE: 70

Leu Thr Tyr Ala Trp His Thr Ser Phe Lys Ala Leu Gly Thr Thr Tyr
1               5                   10                  15

Gln Pro Leu Ser Gly Lys Thr Ser Tyr Xaa
            20                  25

<210> SEQ ID NO 71
<211> LENGTH: 26
<212> TYPE: PRT
<213> ORGANISM: Artificial Sequence
<220> FEATURE:
```

```
<223> OTHER INFORMATION: Synthetic Polypeptide
<220> FEATURE:
<221> NAME/KEY: MISC_FEATURE
<223> OTHER INFORMATION: Generic SMOi2-4
<220> FEATURE:
<221> NAME/KEY: MISC_FEATURE
<222> LOCATION: (1)..(1)
<223> OTHER INFORMATION: wherein LEU at position 1 optionally is
      acetylated
<220> FEATURE:
<221> NAME/KEY: MISC_FEATURE
<222> LOCATION: (5)..(5)
<223> OTHER INFORMATION: wherein X at position 5 is Y, F, or
      4-benzoylphenalalanine (BPA)
<220> FEATURE:
<221> NAME/KEY: MISC_FEATURE
<222> LOCATION: (26)..(26)
<223> OTHER INFORMATION: wherein X at position 26 is K, C, homoCys, Orn,
      diaminobutyric acid (DBA), or diaminopropanoic acid (DPA)
<220> FEATURE:
<221> NAME/KEY: MISC_FEATURE
<222> LOCATION: (26)..(26)
<223> OTHER INFORMATION: wherein X at position 26 optionally is
      palmitoylated

<400> SEQUENCE: 71

Leu Thr Tyr Ala Xaa His Thr Ser Phe Lys Ala Leu Gly Thr Thr Tyr
1               5                   10                  15

Gln Pro Leu Ser Gly Lys Thr Ser Tyr Xaa
            20                  25

<210> SEQ ID NO 72
<211> LENGTH: 24
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<223> OTHER INFORMATION: Generic SMOi2-5
<220> FEATURE:
<221> NAME/KEY: MISC_FEATURE
<222> LOCATION: (1)..(1)
<223> OTHER INFORMATION: wherein TYR at position 1 optionally is
      acetylated
<220> FEATURE:
<221> NAME/KEY: MISC_FEATURE
<222> LOCATION: (3)..(3)
<223> OTHER INFORMATION: wherein X at position 3 is Y, F, or
      4-benzoylphenalalanine (BPA)
<220> FEATURE:
<221> NAME/KEY: MISC_FEATURE
<222> LOCATION: (24)..(24)
<223> OTHER INFORMATION: wherein X at position 24 is K, C, homoCys, Orn,
      diaminobutyric acid (DBA), or diaminopropanoic acid (DPA)
<220> FEATURE:
<221> NAME/KEY: MISC_FEATURE
<222> LOCATION: (24)..(24)
<223> OTHER INFORMATION: wherein X at position 24 optionally is
      palmitoylated

<400> SEQUENCE: 72

Tyr Ala Xaa His Thr Ser Phe Lys Ala Leu Gly Thr Thr Tyr Gln Pro
1               5                   10                  15

Leu Ser Gly Lys Thr Ser Tyr Xaa
            20

<210> SEQ ID NO 73
<211> LENGTH: 13
<212> TYPE: PRT
<213> ORGANISM: Artificial Sequence
<220> FEATURE:
<223> OTHER INFORMATION: Synthetic Polypeptide
<220> FEATURE:
```

```
<221> NAME/KEY: MISC_FEATURE
<223> OTHER INFORMATION: Generic SMOi2-16
<220> FEATURE:
<221> NAME/KEY: MISC_FEATURE
<223> OTHER INFORMATION: wherein each of the amino acids is the D isomer
<220> FEATURE:
<221> NAME/KEY: MISC_FEATURE
<222> LOCATION: (1)..(1)
<223> OTHER INFORMATION: wherein LEU at position 1 optionally is
      acetylated
<220> FEATURE:
<221> NAME/KEY: MISC_FEATURE
<222> LOCATION: (8)..(8)
<223> OTHER INFORMATION: wherein X at position 8 is Y, F, or
      4-benzoylphenalalanine (BPA)
<220> FEATURE:
<221> NAME/KEY: MISC_FEATURE
<222> LOCATION: (13)..(13)
<223> OTHER INFORMATION: wherein X at position 13 is K, C, homoCys, Orn,
      diaminobutyric acid (DBA), or diaminopropanoic acid (DPA)
<220> FEATURE:
<221> NAME/KEY: MISC_FEATURE
<222> LOCATION: (13)..(13)
<223> OTHER INFORMATION: wherein X at position 13 optionally is
      palmitoylated

<400> SEQUENCE: 73

Leu Ala Lys Phe Ser Thr His Xaa Ala Tyr Thr Leu Xaa
1               5                   10

<210> SEQ ID NO 74
<211> LENGTH: 12
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<223> OTHER INFORMATION: Generic SMOi2-17
<220> FEATURE:
<221> NAME/KEY: MISC_FEATURE
<223> OTHER INFORMATION: wherein each of the amino acids is the D isomer
<220> FEATURE:
<221> NAME/KEY: MISC_FEATURE
<222> LOCATION: (1)..(1)
<223> OTHER INFORMATION: wherein ALA at position 1 optionally is
      acetylated
<220> FEATURE:
<221> NAME/KEY: MISC_FEATURE
<222> LOCATION: (7)..(7)
<223> OTHER INFORMATION: wherein X at position 7 is Y, F, or
      4-benzoylphenalalanine (BPA)
<220> FEATURE:
<221> NAME/KEY: MISC_FEATURE
<222> LOCATION: (12)..(12)
<223> OTHER INFORMATION: wherein X at position 12 is K, C, homoCys, Orn,
      diaminobutyric acid (DBA), or diaminopropanoic acid (DPA)
<220> FEATURE:
<221> NAME/KEY: MISC_FEATURE
<222> LOCATION: (12)..(12)
<223> OTHER INFORMATION: wherein X at position 12 optionally is
      palmitoylated

<400> SEQUENCE: 74

Ala Lys Phe Ser Thr His Xaa Ala Tyr Thr Leu Xaa
1               5                   10

<210> SEQ ID NO 75
<211> LENGTH: 11
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<223> OTHER INFORMATION: Generic SMOi2-20
```

```
<220> FEATURE:
<221> NAME/KEY: MISC_FEATURE
<223> OTHER INFORMATION: wherein each of the amino acids is the D isomer
<220> FEATURE:
<221> NAME/KEY: MISC_FEATURE
<222> LOCATION: (1)..(1)
<223> OTHER INFORMATION: wherein LYS at position 1 optionally is
      acetylated
<220> FEATURE:
<221> NAME/KEY: MISC_FEATURE
<222> LOCATION: (6)..(6)
<223> OTHER INFORMATION: wherein X at position 6 is Y, F, or
      4-benzoylphenalalanine (BPA)
<220> FEATURE:
<221> NAME/KEY: MISC_FEATURE
<222> LOCATION: (11)..(11)
<223> OTHER INFORMATION: wherein X at position 11 is K, C, homoCys, Orn,
      diaminobutyric acid (DBA), or diaminopropanoic acid (DPA)
<220> FEATURE:
<221> NAME/KEY: MISC_FEATURE
<222> LOCATION: (11)..(11)
<223> OTHER INFORMATION: wherein X at position 11 optionally is
      palmitoylated

<400> SEQUENCE: 75

Lys Phe Ser Thr His Xaa Ala Tyr Thr Leu Xaa
1               5                   10

<210> SEQ ID NO 76
<211> LENGTH: 26
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<223> OTHER INFORMATION: Generic SMOi2-23
<220> FEATURE:
<221> NAME/KEY: MISC_FEATURE
<222> LOCATION: (1)..(1)
<223> OTHER INFORMATION: wherein the LEU at position 1 optionally is
      palmitoylated.
<220> FEATURE:
<221> NAME/KEY: MISC_FEATURE
<222> LOCATION: (5)..(5)
<223> OTHER INFORMATION: wherein X at position 5 is Y, F, or
      4-benzoylphenalalanine (BPA)
<220> FEATURE:
<221> NAME/KEY: MISC_FEATURE
<222> LOCATION: (26)..(26)
<223> OTHER INFORMATION: wherein X at position 26 is K, C, homoCys, Orn,
      diaminobutyric acid (DBA), or diaminopropanoic acid (DPA)
<220> FEATURE:
<221> NAME/KEY: MISC_FEATURE
<222> LOCATION: (26)..(26)
<223> OTHER INFORMATION: wherein X at position 26 optionally is
      palmitoylated

<400> SEQUENCE: 76

Leu Thr Tyr Ala Xaa His Thr Ser Phe Lys Ala Leu Gly Thr Thr Tyr
1               5                   10                  15

Gln Pro Leu Ser Gly Lys Thr Ser Tyr Xaa
            20                  25

<210> SEQ ID NO 77
<211> LENGTH: 19
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<223> OTHER INFORMATION: SMO-i3-9
<220> FEATURE:
<221> NAME/KEY: MISC_FEATURE
```

```
<222> LOCATION: (1)..(1)
<223> OTHER INFORMATION: wherein ALA at position 1 optionally comprises
      homoCys-palmitate

<400> SEQUENCE: 77

Ala Arg Gly Val Met Thr Leu Phe Ser Ile Lys Ser Asn His Pro Gly
1               5                   10                  15

Leu Leu Ser

<210> SEQ ID NO 78
<211> LENGTH: 16
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<223> OTHER INFORMATION: Penetratin

<400> SEQUENCE: 78

Arg Gln Ile Lys Ile Trp Phe Gln Asn Arg Arg Met Lys Trp Lys Lys
1               5                   10                  15

<210> SEQ ID NO 79
<211> LENGTH: 13
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<223> OTHER INFORMATION: Tat (48-60)

<400> SEQUENCE: 79

Gly Arg Lys Lys Arg Arg Gln Arg Arg Pro Pro Gln
1               5                   10

<210> SEQ ID NO 80
<211> LENGTH: 9
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<223> OTHER INFORMATION: N-term of i2 with X
<220> FEATURE:
<221> NAME/KEY: MISC_FEATURE
<222> LOCATION: (3)..(3)
<223> OTHER INFORMATION: wherein X at position 3 is W, Y, F, or
      4-benzoylphenalalanine (BPA)

<400> SEQUENCE: 80

Tyr Ala Xaa His Thr Ser Phe Lys Ala
1               5

<210> SEQ ID NO 81
<211> LENGTH: 12
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<223> OTHER INFORMATION: SMOi2-21
<220> FEATURE:
<221> NAME/KEY: MISC_FEATURE
<222> LOCATION: (1)..(1)
<223> OTHER INFORMATION: wherein LEU at position 1 optionally is
      palmitoylated
```

```
<220> FEATURE:
<221> NAME/KEY: MISC_FEATURE
<222> LOCATION: (5)..(5)
<223> OTHER INFORMATION: wherein the X at position 5 is BPA
<220> FEATURE:
<221> NAME/KEY: MISC_FEATURE
<222> LOCATION: (12)..(12)
<223> OTHER INFORMATION: wherein the LEU at position 12 optionally
      comprises homocysteine-biotin

<400> SEQUENCE: 81

Leu Thr Tyr Ala Xaa His Thr Ser Phe Lys Ala Leu
1               5                   10

<210> SEQ ID NO 82
<211> LENGTH: 28
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<223> OTHER INFORMATION: SMOi2-29
<220> FEATURE:
<221> NAME/KEY: MISC_FEATURE
<222> LOCATION: (1)..(1)
<223> OTHER INFORMATION: wherein LEU at position 1 optionally is
      actylated
<220> FEATURE:
<221> NAME/KEY: MISC_FEATURE
<222> LOCATION: (24)..(24)
<223> OTHER INFORMATION: wherein the X at position 24 is norleucine

<400> SEQUENCE: 82

Leu Thr Tyr Ala Trp His Thr Ser Phe Lys Ala Leu Arg Gln Ile Lys
1               5                   10                  15

Ile Trp Phe Pro Asn Arg Arg Xaa Lys Trp Lys Lys
            20                  25

<210> SEQ ID NO 83
<211> LENGTH: 28
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<223> OTHER INFORMATION: SMOi2-30
<220> FEATURE:
<221> NAME/KEY: MISC_FEATURE
<222> LOCATION: (12)..(12)
<223> OTHER INFORMATION: wherein the X at position 12 is norleucine

<400> SEQUENCE: 83

Arg Gln Ile Lys Ile Trp Phe Pro Asn Arg Arg Xaa Lys Trp Lys Lys
1               5                   10                  15

Leu Thr Tyr Ala Trp His Thr Ser Phe Lys Ala Leu
            20                  25

<210> SEQ ID NO 84
<211> LENGTH: 14
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<223> OTHER INFORMATION: SMOi2-56
<220> FEATURE:
<221> NAME/KEY: MISC_FEATURE
<222> LOCATION: (12)..(12)
<223> OTHER INFORMATION: wherein the X at position 12 is beta-Ala
```

```
<220> FEATURE:
<221> NAME/KEY: MISC_FEATURE
<222> LOCATION: (13)..(13)
<223> OTHER INFORMATION: wherein the K at position 13 comprises
      AKFSTHWAYTL-beta-Ala attached to its gamma amino group
<220> FEATURE:
<221> NAME/KEY: MISC_FEATURE
<222> LOCATION: (14)..(14)
<223> OTHER INFORMATION: wherein the X at position 14 is K, C, homoCys
      or DBA and optionally is palmitoylated

<400> SEQUENCE: 84

Ala Lys Phe Ser Thr His Trp Ala Tyr Thr Leu Xaa Lys Xaa
1               5                   10

<210> SEQ ID NO 85
<211> LENGTH: 12
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<223> OTHER INFORMATION: Sequence X of Dimer 1
<220> FEATURE:
<221> NAME/KEY: MISC_FEATURE
<223> OTHER INFORMATION: wherein each amino acid is the D isomer
<220> FEATURE:
<221> NAME/KEY: MISC_FEATURE
<222> LOCATION: (1)..(1)
<223> OTHER INFORMATION: wherein the LEU at position 1 optionally is
      acetylated

<400> SEQUENCE: 85

Leu Ala Lys Phe Ser Thr His Trp Ala Tyr Thr Leu
1               5                   10

<210> SEQ ID NO 86
<211> LENGTH: 11
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<223> OTHER INFORMATION: Sequence X of Dimer 2
<220> FEATURE:
<221> NAME/KEY: MISC_FEATURE
<223> OTHER INFORMATION: wherein each amino acid is the D isomer
<220> FEATURE:
<221> NAME/KEY: MISC_FEATURE
<222> LOCATION: (1)..(1)
<223> OTHER INFORMATION: wherein the ALA at position 1 optionally is
      acetylated

<400> SEQUENCE: 86

Ala Lys Phe Ser Thr His Trp Ala Tyr Thr Leu
1               5                   10

<210> SEQ ID NO 87
<211> LENGTH: 10
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<223> OTHER INFORMATION: Sequence X of Dimer 3
<220> FEATURE:
<221> NAME/KEY: MISC_FEATURE
<223> OTHER INFORMATION: wherein each amino acid is the D isomer
```

```
<220> FEATURE:
<221> NAME/KEY: MISC_FEATURE
<222> LOCATION: (1)..(1)
<223> OTHER INFORMATION: wherein the LYS at position 1 optionally is
      acetylated

<400> SEQUENCE: 87

Lys Phe Ser Thr His Trp Ala Tyr Thr Leu
1               5                   10

<210> SEQ ID NO 88
<211> LENGTH: 25
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<223> OTHER INFORMATION: SMOi2-1
<220> FEATURE:
<221> NAME/KEY: MISC_FEATURE
<222> LOCATION: (1)..(1)
<223> OTHER INFORMATION: wherein LEU at position 1 optionally is
      palmitoylated

<400> SEQUENCE: 88

Leu Thr Tyr Ala Trp His Thr Ser Phe Lys Ala Leu Gly Thr Thr Tyr
1               5                   10                  15

Gln Pro Leu Ser Gly Lys Thr Ser Tyr
            20                  25

<210> SEQ ID NO 89
<211> LENGTH: 10
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<223> OTHER INFORMATION: SMO i2-12
<220> FEATURE:
<221> NAME/KEY: MISC_FEATURE
<222> LOCATION: (1)..(1)
<223> OTHER INFORMATION: wherein the THR at position 1 optionally is
      palmitoylated

<400> SEQUENCE: 89

Thr Tyr Ala Trp His Thr Ser Phe Lys Ala
1               5                   10

<210> SEQ ID NO 90
<211> LENGTH: 16
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<223> OTHER INFORMATION: SMOi2-14

<400> SEQUENCE: 90

Val Trp Phe Val Val Thr Tyr Ala Trp His Thr Ser Phe Lys Ala Leu
1               5                   10                  15

<210> SEQ ID NO 91
<211> LENGTH: 15
<212> TYPE: PRT
<213> ORGANISM: Artificial Sequence
<220> FEATURE:
<223> OTHER INFORMATION: Synthetic Polypeptide
```

```
<220> FEATURE:
<221> NAME/KEY: MISC_FEATURE
<223> OTHER INFORMATION: SMOi2-15

<400> SEQUENCE: 91

Trp Phe Val Val Thr Tyr Ala Trp His Thr Ser Phe Lys Ala Leu
1               5                   10                  15

<210> SEQ ID NO 92
<211> LENGTH: 25
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<223> OTHER INFORMATION: SMOi2-57
<220> FEATURE:
<221> NAME/KEY: MISC_FEATURE
<222> LOCATION: (1)..(12)
<223> OTHER INFORMATION: wherein each of the amino acids at positions
      1-12 is the D isomer
<220> FEATURE:
<221> NAME/KEY: MISC_FEATURE
<222> LOCATION: (13)..(13)
<223> OTHER INFORMATION: wherein the LYS at position 13 optionally is
      palmitoylated on the epsilon carbon and optionally is the D isomer

<400> SEQUENCE: 92

Leu Ala Lys Phe Ser Thr His Trp Ala Tyr Thr Leu Lys Leu Thr Tyr
1               5                   10                  15

Ala Trp His Thr Ser Phe Lys Ala Leu
            20                  25

<210> SEQ ID NO 93
<211> LENGTH: 28
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<223> OTHER INFORMATION: SMOi2-58
<220> FEATURE:
<221> NAME/KEY: MISC_FEATURE
<222> LOCATION: (1)..(12)
<223> OTHER INFORMATION: wherein each of the amino acids at positions
      1-12 is the D isomer
<220> FEATURE:
<221> NAME/KEY: MISC_FEATURE
<222> LOCATION: (13)..(13)
<223> OTHER INFORMATION: wherein the LYS at position 13 optionally is
      palmitoylated on the epsilon carbon and optionally is the D isomer

<400> SEQUENCE: 93

Asp Ala Lys Phe Ser Thr His Trp Ala Tyr Thr Leu Lys Pro Ala Leu
1               5                   10                  15

Leu Thr Tyr Ala Trp His Thr Ser Phe Lys Ala Leu
            20                  25

<210> SEQ ID NO 94
<211> LENGTH: 27
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<223> OTHER INFORMATION: SMOi2-59
```

```
<220> FEATURE:
<221> NAME/KEY: MISC_FEATURE
<222> LOCATION: (1)..(12)
<223> OTHER INFORMATION: wherein each of the amino acids at positions
      1-12 is the D isomer
<220> FEATURE:
<221> NAME/KEY: MISC_FEATURE
<222> LOCATION: (13)..(13)
<223> OTHER INFORMATION: wherein the LYS at position 13 optionally is
      palmitoylated on the epsilon carbon and optionally is the D isomer

<400> SEQUENCE: 94

Asp Ala Lys Phe Ser Thr His Trp Ala Tyr Thr Leu Lys Pro Ala Leu
1               5                   10                  15

Leu Thr Tyr Ala Trp His Thr Ser Phe Lys Ala
            20                  25
```